United States Patent [19]
Thornton et al.

[11] Patent Number: 6,015,431
[45] Date of Patent: Jan. 18, 2000

[54] ENDOLUMENAL STENT-GRAFT WITH LEAK-RESISTANT SEAL

[75] Inventors: Troy Thornton, San Francisco; Lilip Lau, Sunnyvale, both of Calif.

[73] Assignee: Prograft Medical, Inc., Palo Alto, Calif.

[21] Appl. No.: 08/773,479

[22] Filed: Dec. 23, 1996

[51] Int. Cl.[7] ........................................................... A61F 2/06
[52] U.S. Cl. ................................... 623/1; 623/12; 606/194
[58] Field of Search .......................... 623/1, 12; 606/108, 606/192, 194, 195

[56] References Cited

U.S. PATENT DOCUMENTS

| | | |
|---|---|---|
| 3,029,819 | 4/1962 | Starks . |
| 3,096,560 | 7/1963 | Liebig . |
| 3,142,067 | 7/1964 | Liebig . |
| 3,805,301 | 4/1974 | Liebig . |
| 3,938,524 | 2/1976 | Sparks et al. . |
| 4,300,244 | 11/1981 | Bokros ........................................... 623/1 |
| 4,512,338 | 4/1985 | Balko et al. . |

(List continued on next page.)

FOREIGN PATENT DOCUMENTS

| | | |
|---|---|---|
| 0551179 | 7/1993 | European Pat. Off. . |
| 0686379 | 12/1995 | European Pat. Off. . |
| 0696447 | 2/1996 | European Pat. Off. . |
| 2678508 | 1/1993 | France . |
| WO95/21592 | 8/1995 | WIPO . |
| WO 96/26695 | 10/1995 | WIPO . |

OTHER PUBLICATIONS

Katzen, B. et al.; "Initial Experience Performing Combined Surgical/Interventional Procedures in the Interventional Suite"; Journal Of Endovascular Surgery—The Official Journal Of The International Society For Endovascular Surgery; 1996; p. 467.

Chuter et al.; "Bifurcated stent–grafts for AAA: 3 year follow–up"; Abstracts from the Seventh International Course on Peripheral Vascular Intervention; J. Endovas. Surg. (1996) p. 458.

Dereume, JP et al.; "Endoluminal Treatment Of Abdominal Aortic Aneurysm with the Corvita Endovascular Graft, Results of a Single–Center, Prospective Feasibility Study of 90 Patients"; Journal Of Endovascular Surgery—The Official Journal Of The International Society For Endovascular Surgery; 1996; pp. 460–461.

Blum, U. et al.; "Dacron Endografts for Infrarenal Abdominal Aortic Aneurysms: 2 Year Follow–Up"; Springer, vol. 20, No. 1; Jan./Feb. 1997.

(List continued on next page.)

Primary Examiner—Bruce E. Snow
Attorney, Agent, or Firm—Morgan & Finnegan LLP

[57] ABSTRACT

An implantable medical device has a tubular member and a sealing member secured to an outer surface of the tubular member. The tubular member is expandable to engage an endolumenal wall and has a lumen for providing an artificial conduit for flow through an endolumenal space defined by that wall. The seal member occludes flow around the tubular member between the outer surface and the endolumenal wall. One suitable tubular member for use in the present invention is a stent-graft which may be bifurcated for use in protecting vascular wall malformations adjacent to vascular bifurcations against endolumenal pressure and flow. The seal member may be a flange that is oriented on the outer surface at one end of the tubular member as a one-way valve against flow. Multiple seal members may be used, either on opposite ends of the tubular member or in series at one end thereof. Where anchors are used to secure the tubular member to the endolumenal wall, the seal member is positioned to protect against flow through leakage paths formed at localized areas of deformation in the tubular wall adjacent to the anchors. One or more seal members may also be used with two or more tubular members to prevent flow through endolumenal spaces that remain open to flow due to gaps between the multiple, parallel tubular members.

23 Claims, 29 Drawing Sheets

U.S. PATENT DOCUMENTS

| | | |
|---|---|---|
| 4,562,596 | 1/1986 | Kornberg . |
| 4,728,328 | 3/1988 | Hughes et al. ............................ 623/12 |
| 4,787,899 | 11/1988 | Lazarus . |
| 4,790,313 | 12/1988 | Borrelly . |
| 4,941,870 | 7/1990 | Okada et al. . |
| 4,994,071 | 2/1991 | MacGregor . |
| 5,100,429 | 3/1992 | Sinofsky et al. . |
| 5,192,289 | 3/1993 | Jessen . |
| 5,232,446 | 8/1993 | Arney . |
| 5,246,452 | 9/1993 | Sinnott . |
| 5,258,042 | 11/1993 | Mehta . |
| 5,271,410 | 12/1993 | Wolzinger et al. . |
| 5,342,387 | 8/1994 | Summers . |
| 5,348,537 | 9/1994 | Wiesner et al. . |
| 5,360,443 | 11/1994 | Barone et al. . |
| 5,370,691 | 12/1994 | Samson . |
| 5,425,739 | 6/1995 | Jessen ...................................... 606/151 |
| 5,489,295 | 2/1996 | Piplani et al. . |
| 5,507,769 | 4/1996 | Marin et al. . |
| 5,522,880 | 6/1996 | Barone et al. . |
| 5,522,881 | 6/1996 | Lentz . |
| 5,522,961 | 6/1996 | Leonhardt . |
| 5,554,182 | 9/1996 | Dinh et al. . |
| 5,562,724 | 10/1996 | Vorwerk et al. . |
| 5,562,727 | 10/1996 | Turk et al. . |
| 5,571,166 | 11/1996 | Dinh et al. . |
| 5,575,815 | 11/1996 | Slepian et al. . |
| 5,628,784 | 5/1997 | Strecker . |
| 5,653,748 | 8/1997 | Strecker . |
| 5,667,523 | 9/1997 | Bynon et al. ............................ 606/198 |
| 5,669,930 | 9/1997 | Igarashi . |
| 5,693,088 | 12/1997 | Lazarus ....................................... 623/1 |
| 5,769,882 | 6/1998 | Fogarty et al. ............................ 623/1 |

OTHER PUBLICATIONS

Katzen et al., "Endovascular therapy of thoracic and abdominal aortic aneurysms" Abstracts from the Seventh International Course on Peripheral Vascular Intervention J. Endovasc. Surg. (1996) 3:467–468.

White et al., "Endoleak following endoluminal repair of AAA: Diagnosis, significance, and management" Abstracts from the Seventh International Course on Peripheral Vascular Intervention J. Endovasc. Surg. (1996) 3:339–340.

Parodi et al., "Long–term follow–up of AAA endoluminal repair" Abstracts from the Seventh International Course on Peripheral Vascular Intervention J. Endovasc. Surg. (1996) 3:335.

Moore et al., "Transfemoral endovascular repair of abdominal aortic aneurysm: Result of the North American EVT phase 1 trial" J. Vasc. Surg. (1996) 23:543–552.

Chuter et al., "Bifurcated stent–grafts for AAA: 3 year follow–up" Fifth International and Interdisciplinary Symposium on Endoluminal Stents and Grafts (Oct. 10–13, 1996) Washinton, D.C., 2 pages total.

*World Medical News*, World Medical Manufacturing Corporation, 13794 NW 4th Street, Bldgs. 210 & 211, Sunrise, Florida, 33325, U.S.A., vol. 5, Issue 3, (Jul. 1996) 3 pages total.

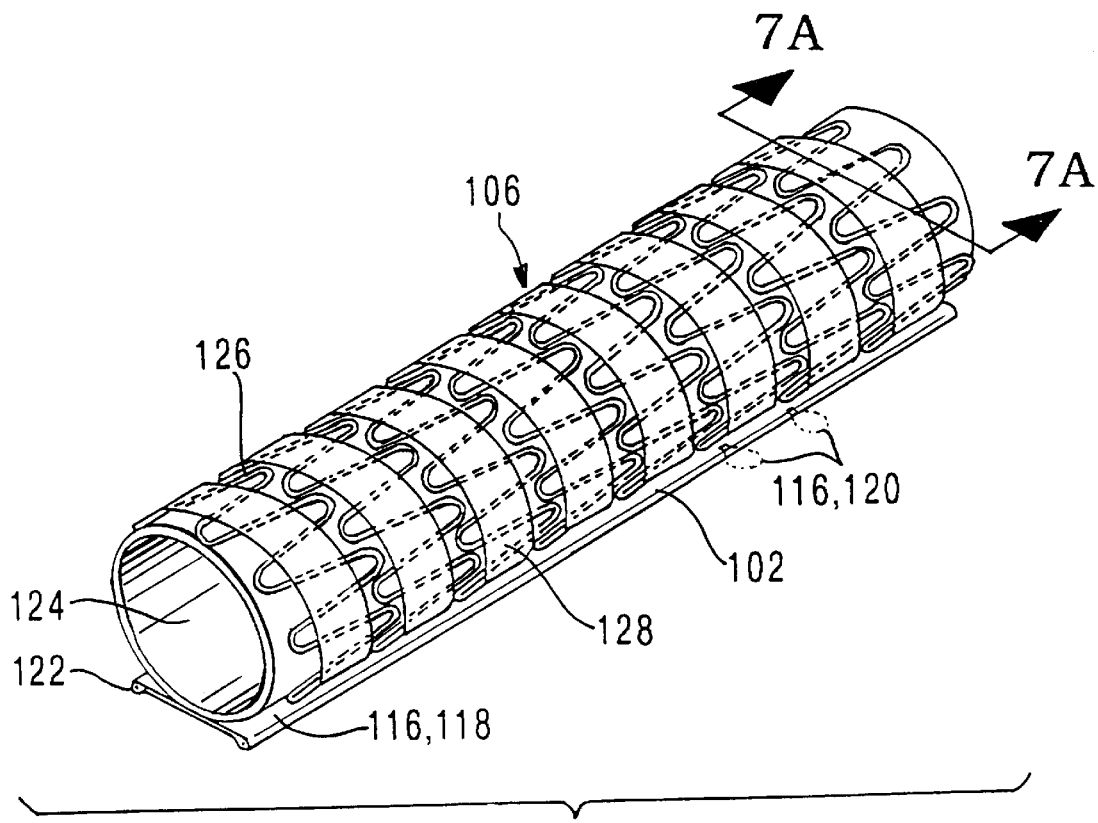
FIG.6
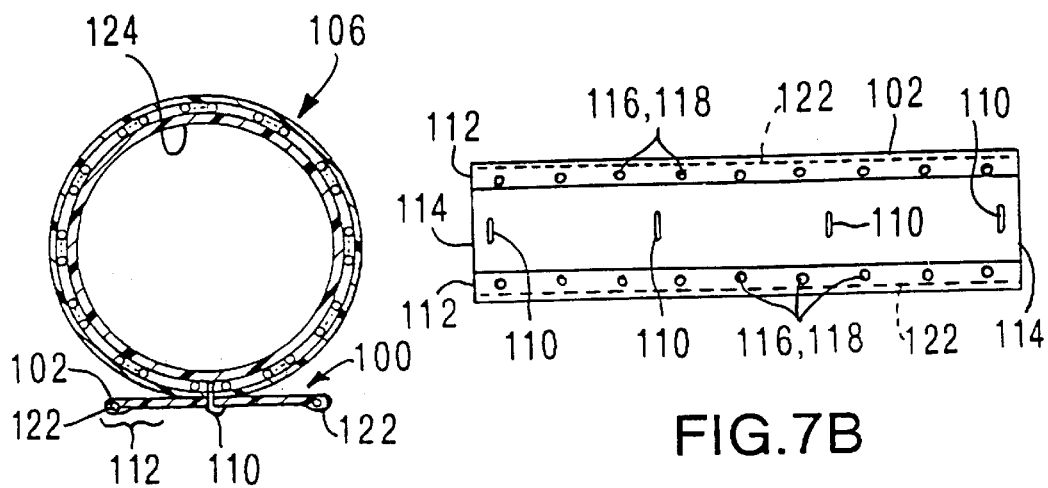
FIG.7A
FIG.7B

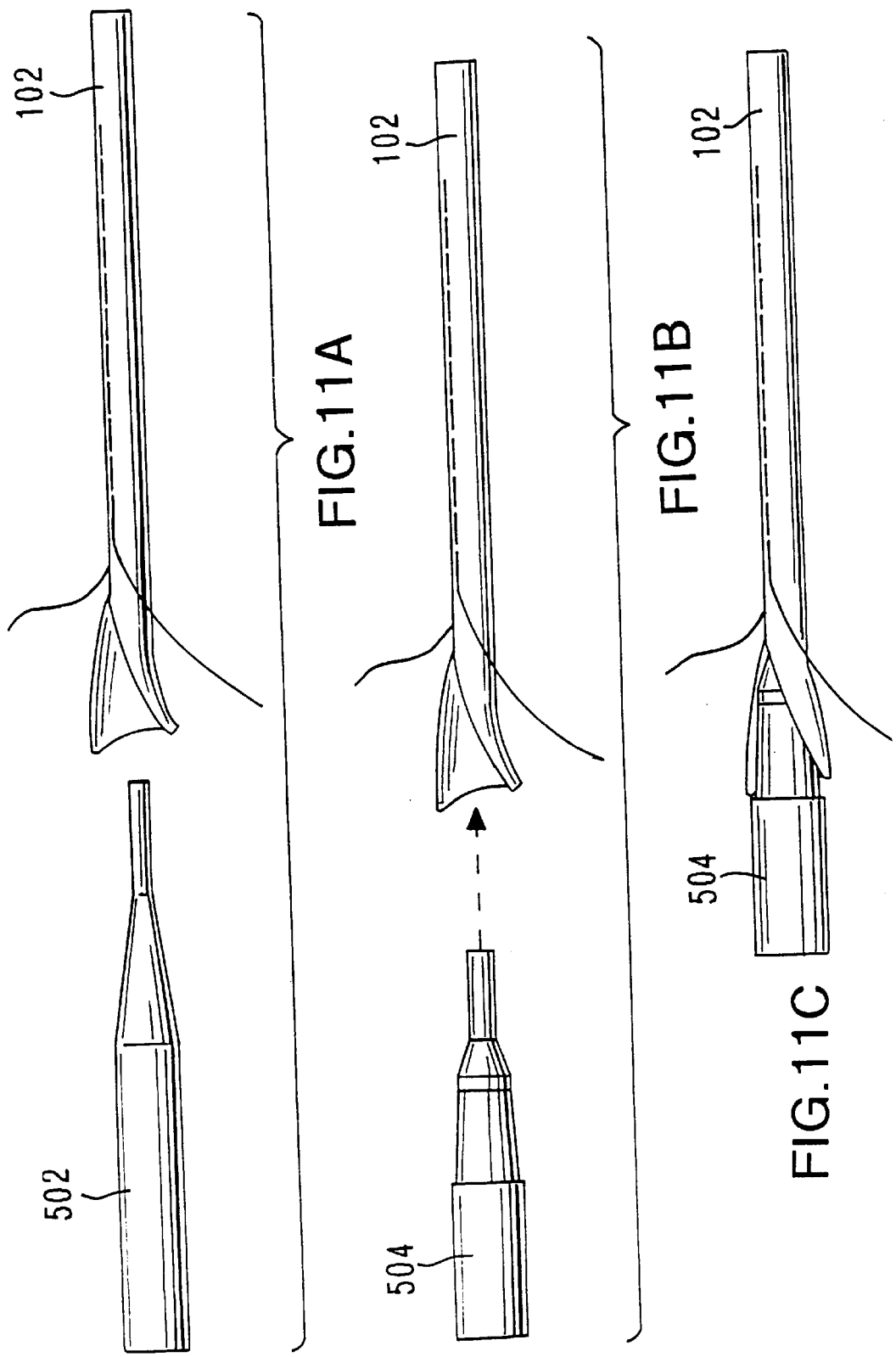

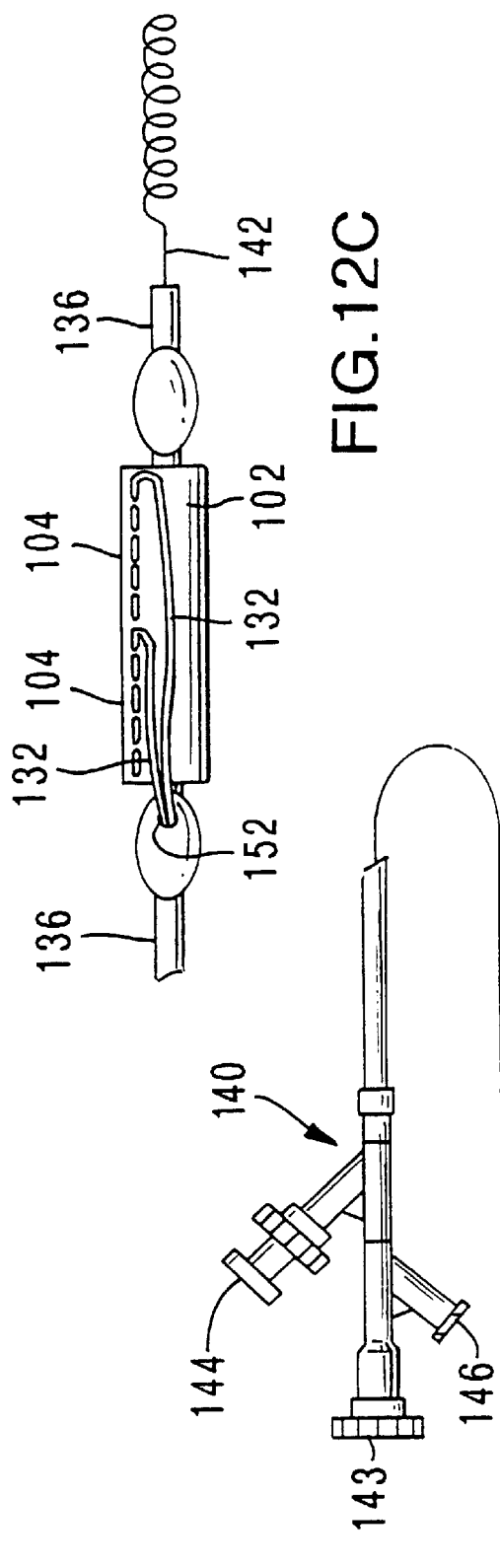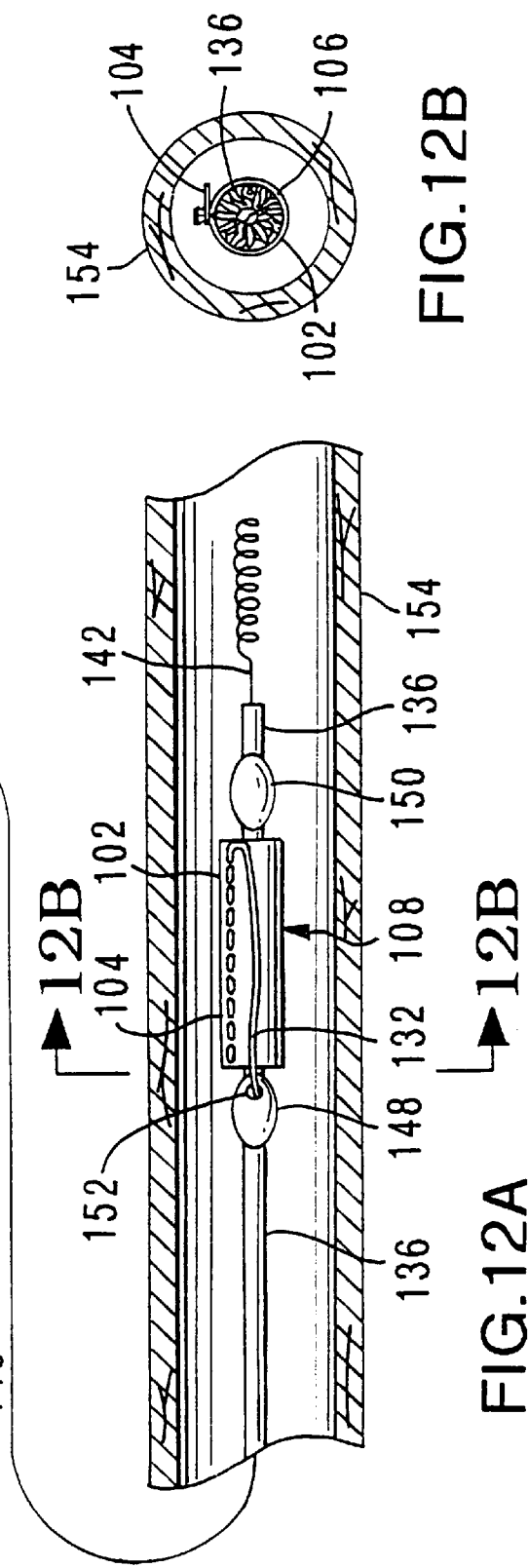

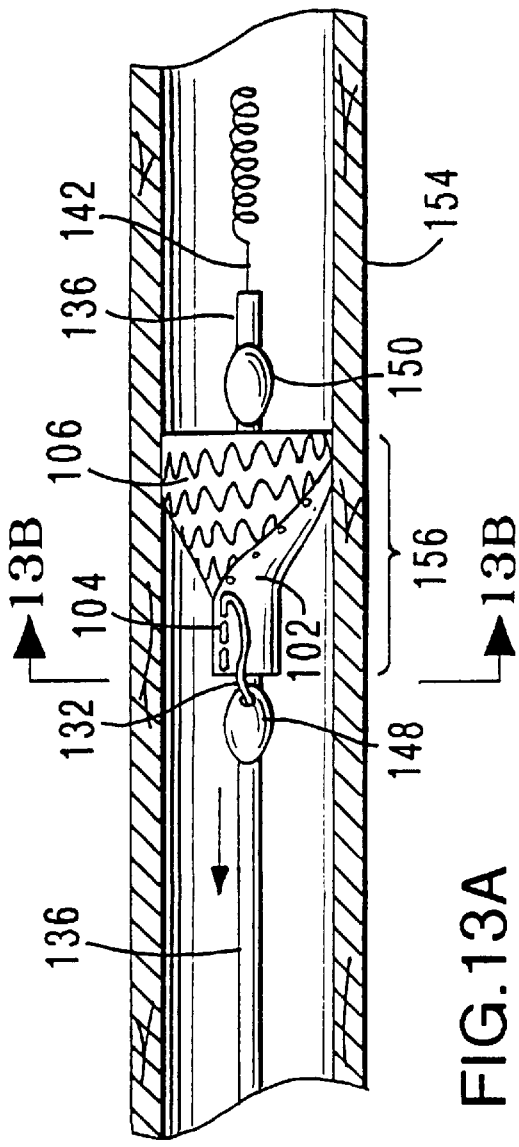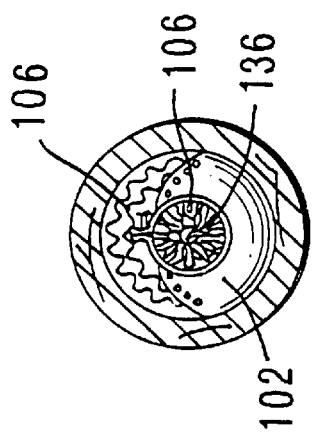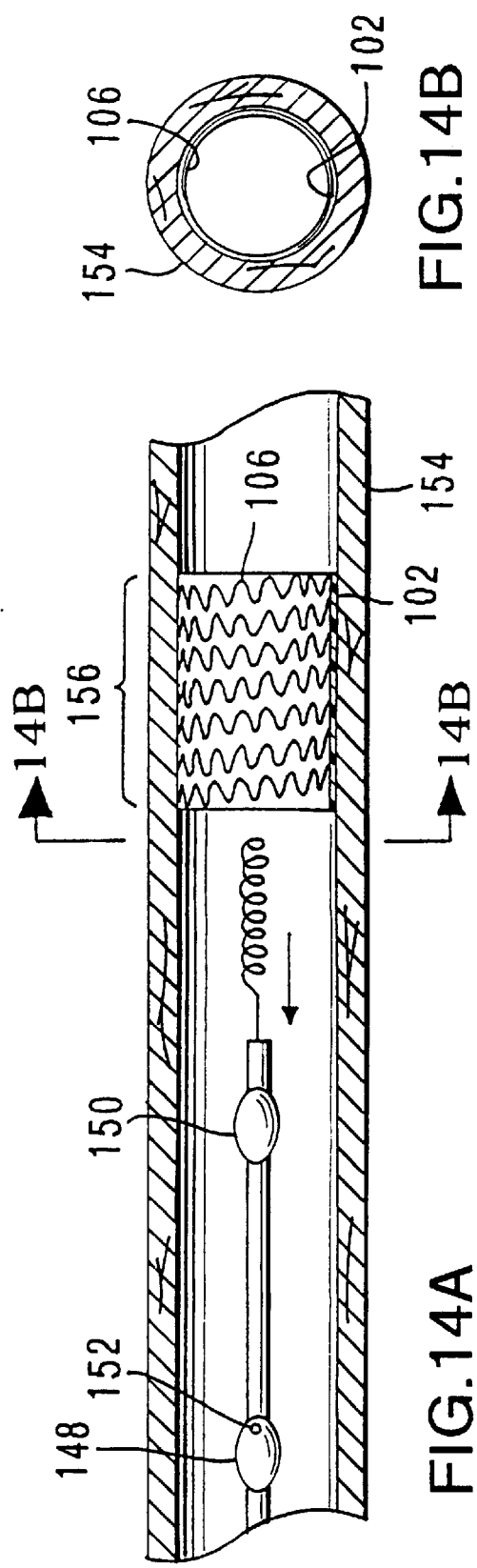

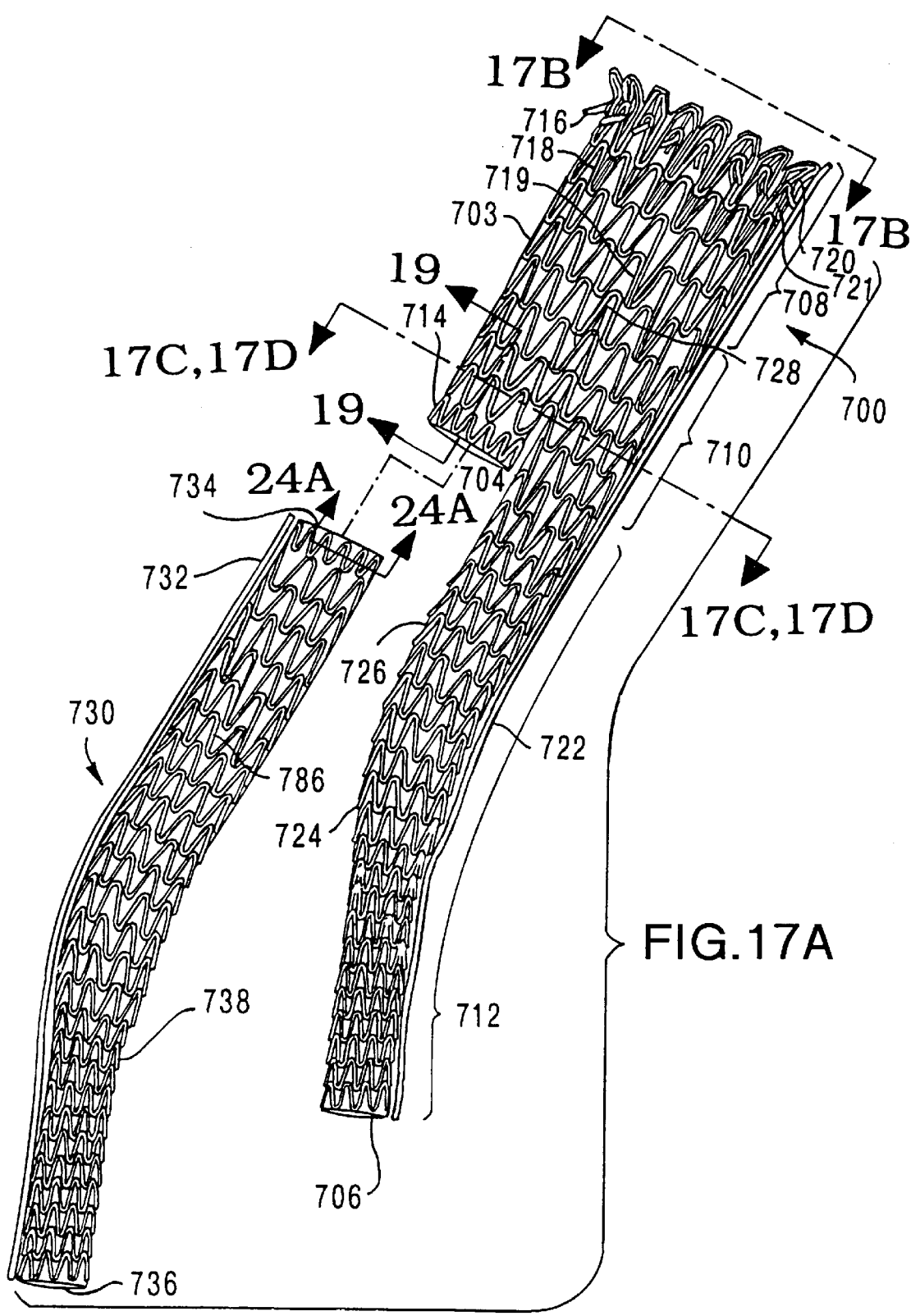

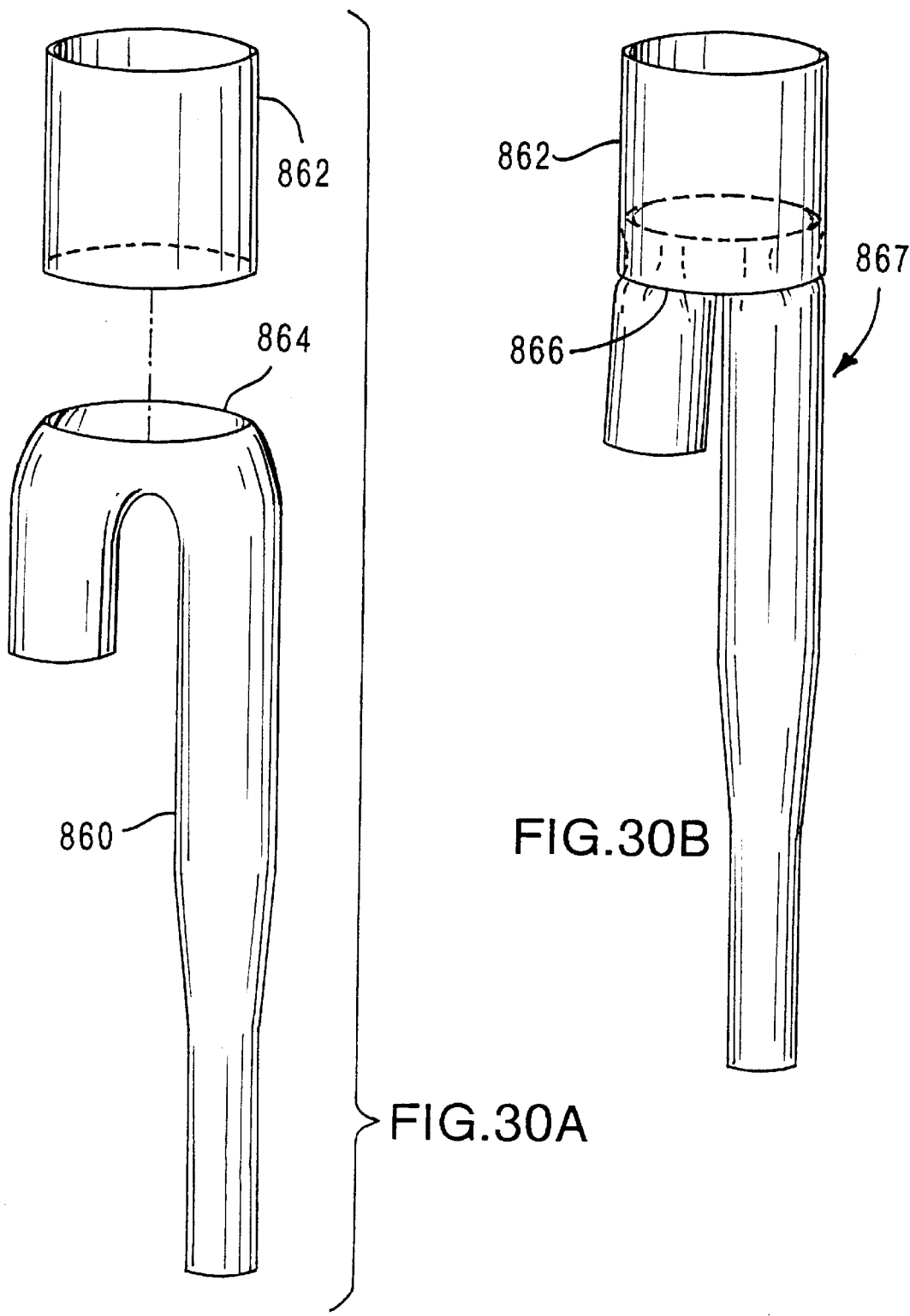

ENDOLUMENAL STENT-GRAFT WITH LEAK-RESISTANT SEAL

TECHNICAL FIELD

This invention is a surgical device assembly. More specifically, it is an implantable medical device for providing an artificial conduit for physiological flow through an endolumenal body space that is defined by an endolumenal wall, and also for substantially isolating that flow from the endolumenal wall.

BACKGROUND ART

Treatment or isolation of vascular aneurysms or of vessel walls which have been thickened by disease has traditionally been performed via surgical bypassing with vascular grafts. Shortcomings of this invasive procedure include the morbidity and mortality associated with major surgery, long patient recovery times, and the high incidence of repeat intervention needed due to limitations of the graft or of the procedure.

Minimally invasive alternatives involving stents or stent-grafts are generally known and widely used in certain types of treatments. Intralumenal stents, for example, are particularly useful for treatment of vascular or arterial occlusion or stenosis typically associated with vessels thickened by disease. Intralumenal stents function to mechanically hold these vessels open. In some instances, stents may be used subsequent to or as an adjunct to a balloon angioplasty procedure.

Stent-grafts, which include a graft layer either inside or outside of a stent structure, are particularly useful for the treatment of aneurysms. An aneurysm may be characterized as a sac formed by the dilatation of the wall of an artery, vein, or vessel. Typically the aneurysm is filled with fluid or clotted blood. The stent-graft provides a graft layer to reestablish a flow lumen through the aneurysm as well as a stent structure to support the graft and to resist occlusion or restenosis.

Treatment of a bifurcation site afflicted with such defects as an occlusion, stenosis, or aneurysm is a particularly demanding application for either stents or stent-grafts. A bifurcation site is generally where a single lumen or artery (often called the trunk) splits into two lumen or arteries (often called branches), such as in a "Y" configuration. For example, one such bifurcation site is found within the human body at the location where the abdominal aortic artery branches into the left and right (or ipsalateral and contralateral) iliac arteries.

When a defect, such as an aneurysm, is located very close to the bifurcation of a trunk lumen into two branch lumens, treatment becomes especially difficult. One reason for this difficulty is because neither the trunk lumen nor either of the branch lumens provides a sufficient portion of healthy, lumen wall on both sides of the defect to which a straight section of single lumen stent or stent-graft can be secured. The stent or stent-graft must span the bifurcation site and yet allow undisturbed flow through each of the branch and trunk lumens.

What is required then is a stent or stent-graft which may be secured to each of the lumen wall a sufficient distance away from the defect and yet is capable of allowing undisturbed flow into each of the branch and trunk lumen. Such a configuration, at least after implantation, generally must have the same Y-shape as described for the bifurcation site. Prior to implantation, the stent or stent-graft may have a Y-shape or may have a modular construction which is assembled into the desired shape as it is implanted.

As we shall see, deployment of implants adapted to meet these needs is also problematic in that they must be deployed and secured in three different lumen which are impossible to access from a single direction. Further, to facilitate intralumenal delivery through a body's tortuous vasculature, the implant must be capable of being compressed into a very small diameter or profile and then expand to a predetermined geometry adapted to engage the vessel wall. However, sometimes this expanded condition is insufficient to completely occlude flow over the device and into the endolumenal defect.

Prior devices that deal with treatment at a bifurcation site within the body generally include grafts, stents, and stent-grafts in either a single-piece or modular configuration.

The use of tubular grafts for treating defects at bifurcation sites has been known for some time. For example, in U.S. Pat. No. 3,029,819 to Starks, U.S. Pat. No. 3,096,560 to Liebig, U.S. Pat. No. 3,142,067 to Liebig, and U.S. Pat. No. 3,805,301 to Liebig. These grafts are typically made of woven fabric or other synthetic material and, because they have no supporting stent structure, typically involve excising the defected segment and suturing the fabric graft in place using common surgical procedures.

A number of bifurcated graft implants have been developed which use some limited means of supporting the one-piece bifurcated graft structure. Examples of such bifurcated grafts include U.S. Pat. No. 4,562,596 to Kornberg; U.S. Pat. No. 5,489,295 to Piplani et al.; and U.S. Pat. Nos. 5,360,443, and 5,522,880, both to Barone et al.

As with all such one-piece devices, the delivery of the graft implant is complicated by the fact that each of the trunk and two legs of the graft must be positioned into their respective lumen and then secured into place. This requires the branch legs to be compressed together for delivery through one of the lumen and requires difficult maneuvering of the branch legs to get them unfolded and untwisted into place within their respective branch lumen. This type of delivery requires the graft sections to be highly flexible so that its components may be manipulated as required and requires a larger profile. This demand for high flexibility often results in unsupported graft sections that may be subject to kinking, folding, collapse or the like.

Bifurcated stent devices have also been disclosed, such as in U.S. Pat. No. 4,994,071 to MacGregor, for example, which discloses a single-piece bifurcated stent for insertion into a bifurcating vessel, or in U.S. Pat. No. 5,342,387 to Summers.

Some implant devices have further used a modular approach, primarily for purposes of enhancing delivery. Examples of modular implants such as stents or grafts include FR 2 678 508 A1; U.S. Pat. No. 5,507,769 to Marin et al; EP 0 (551) (179) A1 to Palmaz et al.; WO 95/(215)92 (International Application number PCT/US95/(014)66); EP (068)6 (379) A2; EP 0 (696) (447) A2; and U.S. Pat. No. 5,562,724 to Vorwerk et al. While these modular devices tend to offer a measure of improved delivery, continuing problems may include a certain amount of leakage around the openings of the device or at the modular connection, as well as increased compressed profiles, and inoptimal flexibility, kink-resistance, and axial stiffness.

Another problem associated with the endovascular repair of aneurysms is postprocedural leakage into the aneurysm sac. Katzen et al., *Initial Experience Performing Combined Surgical/Interventional Procedures in the Interventional*

*Suite* (1996) J. Endovasc. Surg. 3: 467–468, discloses the treatment of patients for abdominal aortic aneurysms (AAAs) using covered (Dacron or polytetrafluoroethylene) multisegment Z-stents; approximately one third of the patients experienced postprocedural leakage. Repair cases of AAAs using the White-Yu endovascular graft were described in White et al., *Endoleak Following Endoluminal Repair of AAA: Diagnosis, Significance, and Management* (1996) J. Endovasc. Surg. 3: 339–340; this technique resulted in leakage around the graft 7.8% of the time. Chuter et al., *Bifurcated Stent-Grafts for AAA: 3-Year Follow-Up* (1996) J. Endovasc. Surg. 3:453, describes the observation of persistent perigraft leakage 12% of the time in a late portion of patients treated for an AAA using a bifucated stent-graft. Parodi et al. *Long-term Follow-up of AAA Endoluminal Repair* (1996) J. Endovasc. Surg. 3:335, cites leakage as one of the primary factors causing early failures of aortic tube graft replacement treatment of AAAs, employing either proximal stent fixation or aortoiliac stent grafts; perigraft leakage is the only cited cause in late failures.

The postprocedural leakage problem has persisted in more recently developed systems for AAA treatment. Moore et al., in *Transfemoral Endovascular Repair of Abdominal Aortic Aneurysm: Results of the North American EVT Phase 1 Trial* (April 1996) J. Vasc. Surg., 543–552, disclose an endovascular grafting system (EGS) consisting of an endovascular prosthesis, an endovascular deployment assembly, and an expandable introducer sheath developed by Endovascular Technologies for the treatment of AAAs. Moore et al. discloses postprocedural leakage for this device, as initially detected, in 44% of the patients; persistent leakage was observed in greater than 20% of the patients.

An endovascular grafting system is further described in Dereume et al. *Endoluminal Treatment of Abdominal Aortic Aneurysm with the Corvita Endovascular Graft. Results of a Single-Center, Prospective Feasibility Study of 90 Patients* (1996) J. Endovasc. Surg. 3:453–483. Dereume et al. describe a system composed of a metallic self-expanding braided wire stent and an inner liner comprised of polycarbonate urethane microfibers. Among patients treated with this graft, 38% presented some postprocedural leakage, according to the Dereume et al. disclosure.

In short, the prior art does not disclose a system for the endovascular repair of AAAs that has adequately addressed the problem of postprocedural leakage.

From the foregoing discussion it is evident that it would be desirable to have a stent-graft device for treating vessel wall aneurysms by endolumenally isolating the abnormal aneurysmal wall from blood pressure, and which does not allow for substantial leakage flow around the outer periphery of the device.

SUMMARY OF THE INVENTION

The present invention is an implantable medical device for delivery to an endolumenal body space that is defined by an endolumenal wall and for providing an artificial conduit for flow through the endolumenal body space. The device preferably is adapted for delivery to an intravascular region of an aneurysm and provides a conduit through that region while protecting the aneurysm from the intralumenal pressure.

In one variation of the invention, the implantable medical device has a tubular member and a sealing member.

The tubular member has a tube wall with a length, two opposite end portions with a central portion therebetween, and an outer surface. The outer surface has a diameter and shape dimensioned to substantially engage at least a portion of the endolumenal wall. Furthermore, the tubular wall defines a lumen that extends along the length and that provides a conduit for flow through the endolumenal body space.

The seal member is secured to the outer surface and is adapted to occlude leakage flow externally around the tubular wall between the outer surface and the endolumenal wall when the tubular member is deployed within the endolumenal body space.

In one mode of this variation, the seal member is an occlusive cuff that forms a flange as a one-way valve over the conduit tubing member's outer surface.

In another mode, the tubular member has a radially collapsed condition such that the outer surface has a reduced diameter which is dimensioned to be smaller than the endolumenal diameter. The tubular member of this mode is adjustable to a radially expanded condition such that the outer surface has the first diameter and shape for engaging the endolumenal wall. This mode allows for delivery of the tubular member when in the radially collapsed condition, and implantation of the tubular member when in the radially expanded condition.

In still another mode of this variation, the tubular member includes an anchor and the seal member is adjacent to that anchor. It is believed that the anchoring of endolumenal grafts may create leakage paths around the outer surface of the graft. The seal member is positioned to occlude such leakage paths.

Another variation of the invention is an implantable medical device that has a tubular member, which is a stent-graft, in combination with a seal member over the outside surface of that stent-graft. The stent graft includes a flexible, tubular graft member, and also a stent member which is coupled to an outer surface of the tubular graft member. The stent member has at least one circumferentially reinforcing member that is constructed of relatively rigid material compared to the tubular graft member.

In a further mode of this variation, the stent-graft which makes up the tubular member is bifurcated, which provides primary utility for implantation in lower abdominal aortic bifurcations which have aortic wall aneurysms. It is believed that leakage into aneurysms over bifurcated implants of this type may occur over either the main body end, or over one or both of the legs of the bifurcation. Therefore, the seal member may be positioned adjacent the distal end of the main body of this stent-graft, or adjacent the end of one of the legs of the bifurcation, or both.

BRIEF DESCRIPTION OF THE DRAWINGS

FIG. 6 is a perspective view of the assembly of FIG. 4 with the restraint released and the implant in an expanded state.

FIG. 7A is an end view of the assembly of FIG. 6.

FIG. 7B is a bottom plan view of the restraining member of FIG. 7A.

FIGS. 11A, 11B, 11C, 11D, 11E and 11F diagrammatically show a procedure for loading an expandable stent-graft into a restraining member prior to endolumenal delivery.

FIG. 12A diagrammatically shows delivering a restrained implant to a desired site in a mammalian body lumen with the coupling member configured as shown in FIGS. 10A–10C.

FIG. 12B is a sectional view of FIG. 12A taken along line 12B—12B.

FIG. 12C shows an alternate multiple restraining member arrangement for that shown in FIG. 12A.

FIG. 13A diagrammatically shows partial deployment of the implant assembly illustrated in FIG. 12A showing progressive expansion in a direction away from the distal end of the illustrated guidewire (i.e., toward the illustrated hub).

FIG. 13B is a sectional view of FIG. 13A taken along line 13B–13B.

FIG. 14A diagrammatically shows full deployment of the implant assembly illustrated in FIG. 12A.

FIG. 14B is a sectional view of FIG. 14A taken along the line 14B—14B.

FIG. 17A is a perspective view of a bifurcated stent-graft.

FIG. 30A is a front view of the unassembled components of an alternate construction of the graft element.

FIG. 30B is a front view of the assembled graft element according to the alternative construction of FIG. 30A.

BRIEF DESCRIPTION OF THE EMBODIMENTS

The present invention is an implantable medical device assembly which has a tubular member designed to engage a length of endolumenal wall that defines an endolumenal space, and which has a seal member on the outer surface of the tubular member that occludes flow around the tubular member between its outer surface and the endolumenal wall.

It is believed that this invention is particularly useful when the seal member is secured to the outer surface of a stent-graft as the tubular member. This variation is particularly useful in the treatment of intravascular aneurysms, wherein the seal member occludes leakage flow around the stent-graft and substantially isolates that flow from the dangerous, abnormal aneurysmal wall. It is further believed that the broad aspects of tubular member-seal member combination of the invention has utility in the prevention of leakage flow around the outer surfaces of implantable endolumenal medical devices.

Figure 1:
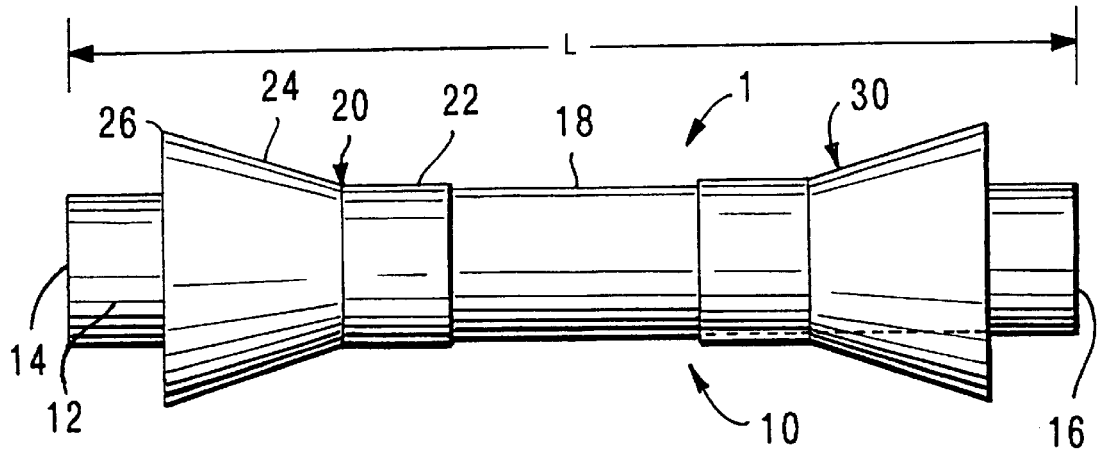
FIG. 1 is a perspective view of an implantable medical device of the present invention wherein a seal member is secured to an outer surface of a tubular member adjacent an end of the tubular member.

A first implantable medical device (1) variation of the present invention is depicted in FIG. 1, which shows tubular member (10) and seal member (20) secured to tubular member (10).

Tubular member (10) is shown in FIG. 1 to include a tubular wall (12), which has a length L defined by two opposite end portions (14, 16) and central portion (15) between those end portions. Tubular wall (12) also defines a lumen which extends along length L, and further includes an outer surface (18).

Seal member (20) is shown in FIG. 1 as an occlusive cuff, which has a first cuff end (22) secured to outer surface (18) of tubular wall (12), and which also has a second cuff end (24) at least a portion which is unsecured to form a flange (26). In this configuration, flange (26) forms a one-way valve that circumferentially surrounds tubular member (10) and occludes flow around tubular wall (12) in the direction from the first cuff end (22) to the second cuff end (24) when tubular member (10) is deployed within a radially confining endolumenal space.

More particularly in FIG. 1, flange (26) is shown in a flared condition, which condition may be its relaxed geometry or may be a geometry imparted thereto by flow in the occluded direction. In the case where the flared shape of flange (26) is its relaxed geometry, flange (26) may include an outward bias to that shape, such that when tubular member (10) is deployed into an endolumenal space (not shown in FIG. 1), flange (26) may engage a radially confining endolumenal wall defining that space (not shown) and thereby enhance the reduction of flow around tubular member (10) between outer surface (18) and the endolumenal wall.

In one construction, both tubular wall (12) and seal member (20) comprise heat compatible polymers, such that seal member (20) may be secured to tubular wall (12) with a heat seal. In one mode of this construction, only first cuff end (22) may be brought into contact with outer surface (18) and the heat seal is formed upon generally heating the region of seal member (20). In another mode, seal member (20) may be a heat shrinkable polymeric material, such as a material chosen from the group consisting of fluoropolymers, cross-lined polyolefins such as cross-linked polyethylene, polymides, or combinations thereof. In this mode, heat may be applied only to one end of the seal member (20), which shrinks in response thereto and melts to the tubular member (10).

It should be further understood that seal member (20) could be secured to outer surface (18) in a variety of ways other than a heat seal, as would be apparent to one of ordinary skill. For example, an appropriate adhesive for the materials chosen for seal member (20) and tubular member (10) may be used to make an adhesive bond therebetween. Alternatively, seal member (20) may have a friction fit over outer surface (18), as may be the case when seal member (20) is heat shrunk onto outer surface (18) but is not actually melted to that surface. This may be the case, for instance, when seal member (20) and tubular member (10) do not comprise heat compatible polymers. Furthermore, some mechanical coupling may secure seal member (20) to outer tube member (10).

An additional seal member (30) is also shown in FIG. 1 on opposite end portion (16) and secured in an opposite orientation along the longitudinal axis of tubular member (10) when compared to seal member (20).

Figure 2:
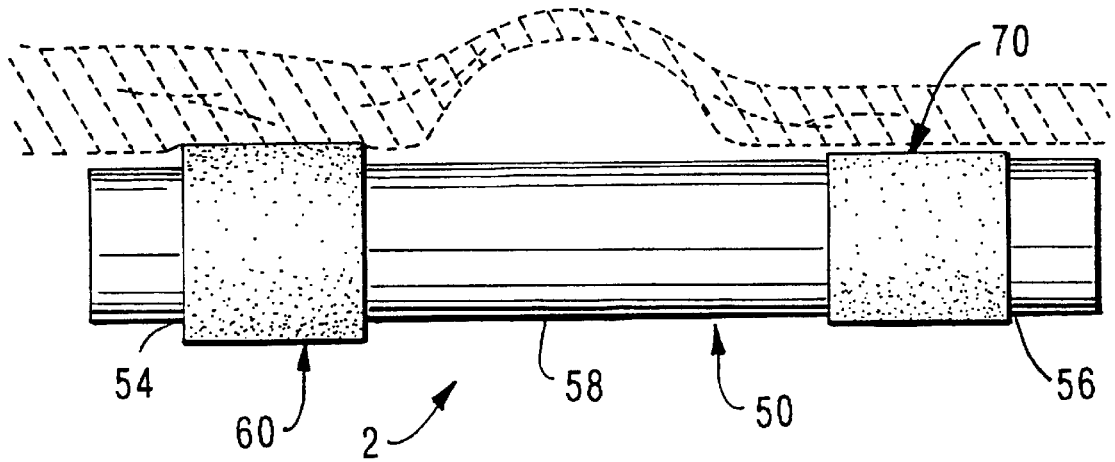
FIG. 2 is a perspective view of a further embodiment of the implantable medical device of FIG. 1, wherein two similar seal members are shown secured to outer surfaces of two opposite end portions of the tubular member with one seal member in an expanded condition relative to the other seal member.

Alternatively to the flange/one-way valve variation of FIG. 1, FIG. 2 shows implantable medical device (2) to include two similar seal members (60,70) which are expandable from a first diameter to a second diameter, and which are secured to the outer surfaces of two opposite end portions (54,56) of tubular wall (50). For purposes of illustration in FIG. 2, seal member (60) is shown in an expanded condition relative to unexpanded seal member (70).

In one preferred construction, seal members (60,70) comprise a hydrophilic material, preferably a hydrophilic polymer or gel-foam, which expands when exposed to water, such as in blood or other water-containing body fluids, and which is adherent to outer surface (58) of tubular wall (50), as would be apparent to one of ordinary skill. In the variation employing this construction, the hydrophilic material has an initially low profile prior to the implantable medical device being deployed into the endolumenal space where seal members (60,70) are exposed to hydrophilic body fluids or other artificially introduced fluids therein. Upon exposure to such fluids, the seal members (60,70) absorb water and expand outwardly from outer surface (58) to create an occlusive effect to flow across the seal members (60,70).

While particular variations of the seal member of the present invention are herein described such as in FIGS. 1 and 2, it is to be further appreciated by one of ordinary skill that other seal member variations may be secured to outer surfaces of implantable endovascular medical devices without departing from the scope of the invention. For example, a thrombogenic material such as collagen or Dacron fibers may be secured to an outer surface of an implantable endolumenal medical device and suitably occlude flow around that device for a particular medical application. However, clinical limitations, such as profile, lubricity, traumaticity, or toxicity may dictate the utility of a particular seal member when it is intended to be combined with a tubular member which is designed for a particular application.

It is to be understood that one seal member may be used in the current invention, or two seal members may be used on opposite end portions of the tubular member to form a "dual-seal," as is shown in FIGS. 1 and 2 for purposes of illustration. The scope of either variation should be considered to include both seal member variations of FIGS. 1 and 2, as well as other seal member variations that would be apparent to one of ordinary skill.

It is believed that, when the implantable medical device is deployed within high pressure vessels such as the aorta, the pressure drop across the outer surface of the tubular wall is high enough at each end portion to cause leakage flow into the central portion of the tubular member. In the "dual seal" variation of the present invention, such as that shown in FIG. 2, both of these potential leakage paths are occluded. In design variations for treating aortic aneurysms, such as lower abdominal aneurysms, the "dual-seal" variation may be a highly desirable design for this reason.

Furthermore, in either case of one end or both ends including a seal member, there may also be a multiplicity of such seal members on a single end. For example, more than one seal member such as seal member (20) in FIG. 1 may be used in series on a single end of the tubular member, such as for the purpose of providing a redundancy of safety. If, for example, one of the serial seal members fails to provide a sufficient seal, such as for reasons of anatomical abnormalities at that seal, another serial seal member may be properly engaged to the endolumenal wall and provide the necessary obstruction to leakage flow.

A further embodiment of the present invention also contemplates use of seal members, such as seal member (20) in FIG. 1, with multiple tubular members to be placed in parallel within an endolumenal space.

In one variation of this embodiment, two parallel tubular members such as tubular member (10) in FIG. 1 may be wrapped together with one circumferential cuff. In one construction of this variation, the first cuff end is constricted or heat shrunk to conform to the crease between the outer circumferential surfaces of the parallel tubular members. The other, second cuff end is left unsecured to form the flange, wherein the first and second cuff ends for the one-way valve against flow along and between the outer surfaces of the two parallel tubular members.

In a further variation, each parallel tubular member may have its own seal member secured thereon and still provide suitable flow obstruction, particularly in combination with the other, parallel tube with seal member. For example, when such seal members are constructed with a flare, such as shown for seal members (20) and (30) in FIG. 1, they may meet at the "inter-tubular" spaces and thereby form a cross-sectional obstruction against flow through those spaces.

Therefore, according to the multiple seal member variations just described, all of the embodiments of the invention should be contemplated to include these variations, even in cases where there may be only one seal member shown on one end portion of a tubular member.

Figure 3:
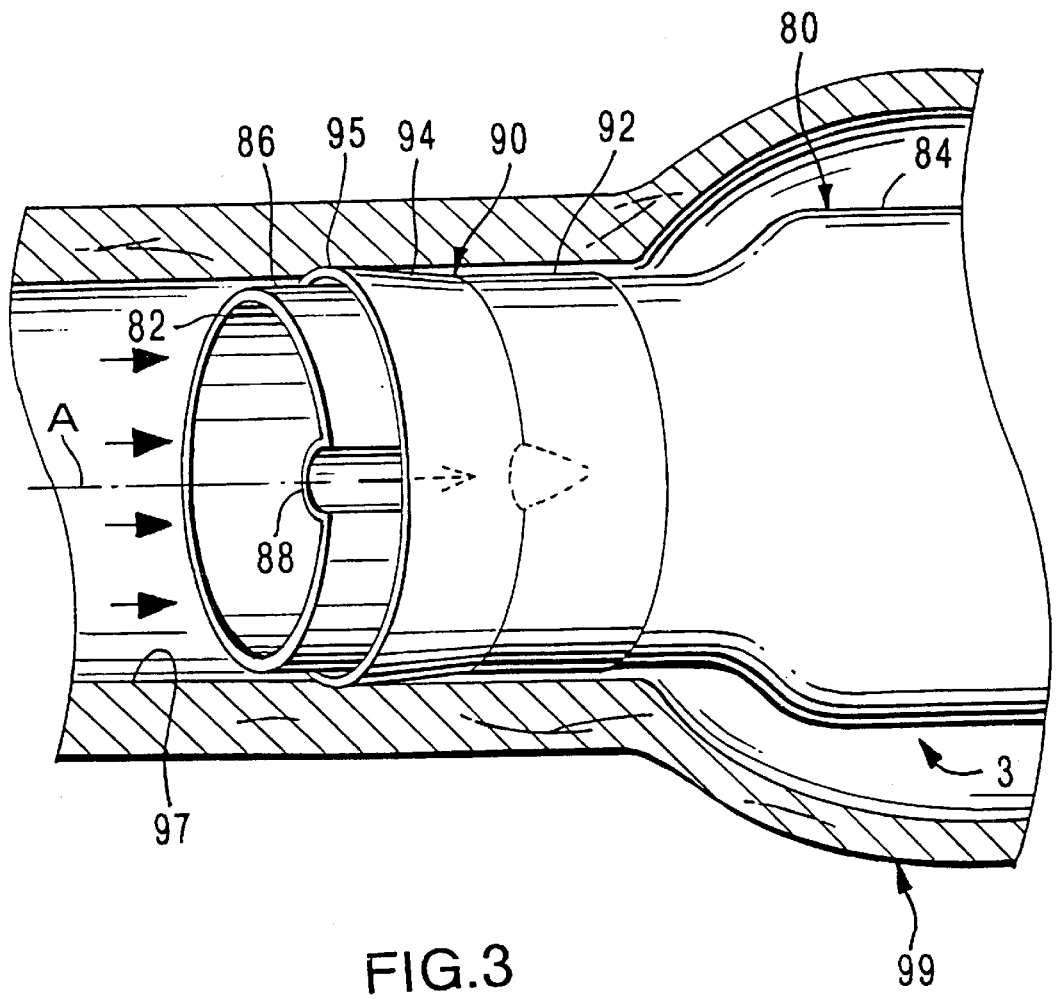
FIG. 3 is a perspective view of the implantable medical device of FIG. 1, wherein the tubular member is shown in a radially expanded position within an intravascular region of an aneurysm.

FIG. 3 further shows the use of one variation of the present invention, which is believed to be particularly useful for the treatment of intravascular aneurysms. Implantable medical device (3) is depicted in FIG. 3 with tubular member (80) and seal member (90) deployed within an intravascular region of aneurysm (99).

Tubular member (80) includes an expandable tubular wall (82) having one end portion (86) engaged with a vascular wall (97) at a location adjacent to aneurysm (99). Tubular member (80) also includes another opposite end portion which similarly engages vascular wall (97) on the opposite transverse side of aneurysm (99) relative to the vessel's longitudinal axis (not shown). A central portion (84) of tubular member (80) is located between the tubular member's opposite end portions and is shown in FIG. 3 in partial view. Central portion (84) has a length and an expanded diameter sufficient to substantially span the abnormal wall section that comprises aneurysm (99) (not shown).

In one desirable construction, tubular member (80) may comprise a stent-graft which is deliverable to the intravascular region of the aneurysm (99) in a radially collapsed condition and which is adjustable to the radially expandable condition shown in FIG. 3. Such radial adjustment may be actuated by balloon expansion of the stent-graft structure, or the stent-graft structure itself may be self-expanding, such as upon removing a radially confining member from the stent-graft which has a bias to the radially expanded shape. Variations of a particularly desirable stent-graft embodiment are provided in detail in FIGS. 14A–32D.

Seal member (90) is shown in FIG. 3 to be secured to an outer surface of end portion (86). Seal member (90) is an occlusive cuff of a similar type to that shown in FIG. 1, wherein first cuff end (92) is secured to the outer surface of tubular member (80) and second cuff end (96) is unsecured to form a flange (95). The particular orientation shown for the adjacent first and second cuff ends (92,94) along the longitudinal axis A of end portion (86) allow for flange (95) to provide a one-way valve against flow in the direction from end portion (86) toward central portion (84). Tubular member (80) thus provides an artificial conduit for flow through the region of aneurysm (99) (shown with representative arrows) and aneurysm (99) is substantially isolated from leakage flow across the one-way valve of seal member (90).

Tubular member (80) is further shown in FIG. 3 in a radially expanded condition wherein the outer surface of the tubular wall (82) has a dimension and shape sufficient to engage wall (97). In fact, the expanded condition is actually shown here to be oversized, which is often desired in order to effectuate enough force at the wall to hold the tubular member (80) in its deployed position along the longitudinal axis of lumen (97). However, in such a design, a wrinkle such as wrinkle (88) may result due to the under-expanded state of the tubular member. This may present a leakage path to allow flow to propagate along the outer surface of tubular member (80) and into aneurysm (99). Seal member (90), however, is shown to be positioned with flange (95) over a portion of that wrinkle (88) and with first cuff end (92) secured over the outer surface of the end of the leakage path which is wrinkle (88). In this mode, the leakage path is occluded and any flow that would otherwise propagate therethrough is captured by flange (95).

The following portions of the description relate to FIGS. 4–32D, and are directed toward variations of two highly desirable embodiments of the present invention. The particular embodiment of FIGS. 4–16 relates to variations of a particular assembly for delivering the implantable medical device of the present invention when the tubular member of the device is self-expanding from a first radially collapsed condition to a second radially expanded condition. The particular embodiment of FIGS. 17–32D relates to variations of a particular tubular member construction for the implantable medical device of the present invention, which tubular member construction is a highly desirable, modular stent-graft.

Corset Delivery of Implantable Medical Device

Referring to drawings 4–16 in detail wherein like numerals indicate like elements, delivery systems for delivering implants or devices, such as stents or stent-grafts, to a desired site in mammalian vasculature are shown. The delivery systems of the present invention generally include a restraining member that is adapted and configured for surrounding at least a portion of a collapsed or compressed implant and a coupling member(s) for releasably coupling portions of the restraining member to one another to maintain the implant in its collapsed or compressed state.

Figure 4:
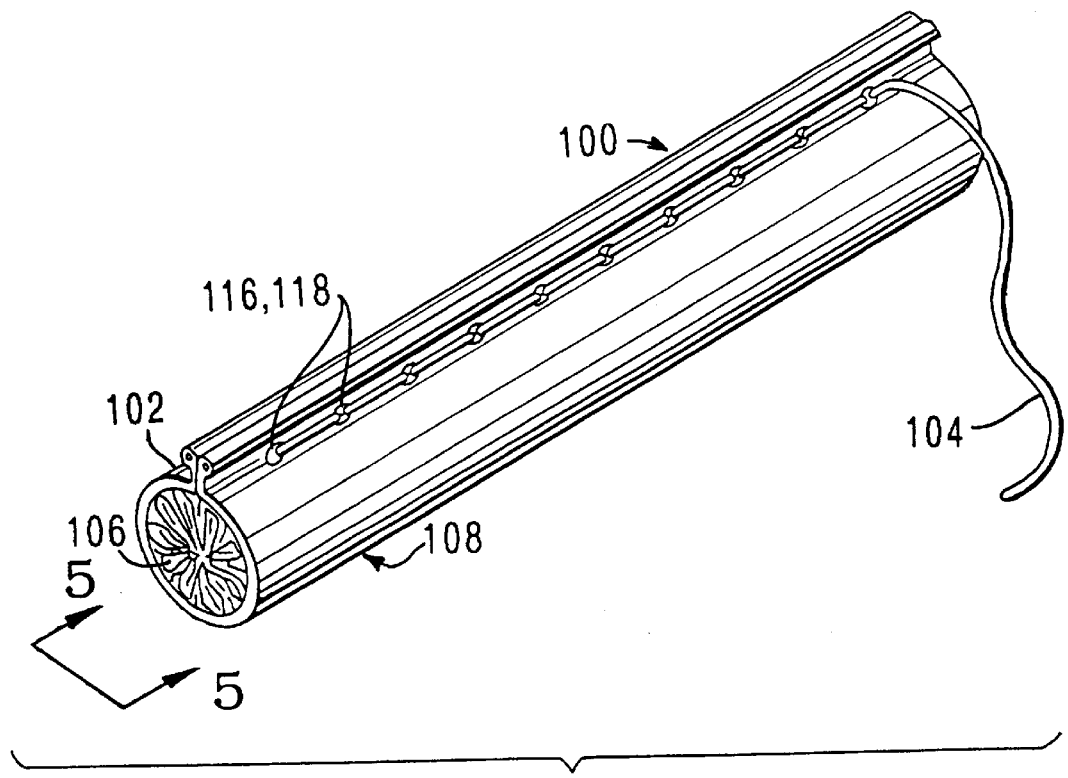
FIG. 4 is a perspective view of an implantable medical device that is restrained in a collapsed state.
Figure 5:
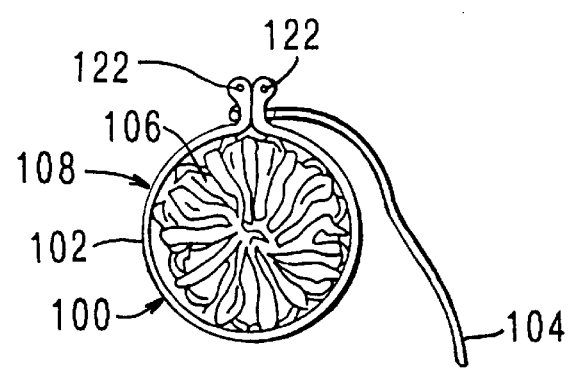
FIG. 5 is an end view of the restrained implant of FIG. 4.

Referring to FIGS. 4–7, an implant delivery system suitable for use with the present invention is shown. Delivery system (100), generally includes a restraining member (102), which as shown may be in the form of a sheet of material, and a coupling member (104) for releasably coupling portions of the restraining member to one another. The restraining member portions that are coupled may differ from those illustrated, but preferably are selected to maintain the implant, such as self-expanding stent-graft (106), in a collapsed or compressed state as shown in FIGS. 4 and 5 where the restraining member (102) is shown in the form of a tube. In the illustrative variation, the coupling member (104) is shown as a filament or thread-like element which prevents the restraining member (102) from rearranging to a configuration where the stent-graft (106) could expand to its expanded state.

The implant may be collapsed in any suitable manner for placement within the restraining member (102). For example, the implant may be folded or radially crushed before placement within the restraining member (102) as will be described in more detail below. As shown in FIGS. 12–14, a delivery assembly (108), which includes the restraining member (102) and the stent-graft (106), has relatively small cross-sectional dimensions which facilitate endolumenal delivery of the assembly to a site where the natural lumen diameter may be smaller than the expanded diameter of the stent-graft (106).

Referring to FIGS. 6 and 7A, the assembly (108) is shown in a deployed state after removal of the coupling member (104). The restraining member (102) may be fixedly secured to the stent-graft (106) so that the two components remain attached after expansion at the desired deployment site. Two or more sutures (110) may be used to fixedly attach the restraining member (102) to the stent-graft (106) as shown in FIGS. 7A and 7B. Although one arrangement of the sutures (110) is shown in FIG. 7B other arrangements may be used. The attachment between the restraining member and the implant preferably is made to prevent significant movement between the restraining member and stent-graft after deployment which could disrupt endovascular fluid flow.

Although other configurations of the restraining member (102) can be used, a preferred configuration is a generally rectangular one as shown in FIG. 7B. The restraining member configuration may vary depending on the confirmation of the implant. For example, in the case where the restraining member is used in conjunction with a modular bifurcated stent as will be described below, the restraining member may have a similar rectangular configuration as that shown in FIG. 7B, one that have two differently sized rectangular portions arranged to mate with the regions of different diameter (trunk and leg) or another configuration that would maintain the implant in a collapsed stent when secured. Returning to FIG. 7B, the restraining member may be described as having side margins (112) that extend between the ends (114) of the member. Eyelets (116) are disposed along the side margins so that the coupling member (104) may be laced or threaded therethrough. The eyelets may be in the form of through holes (118), which may be formed by a uniform-diameter puncturing device or by other means such as laser-drilling. Alternatively, the eyelets may be formed by loops (120) which may be attached to the side margins (112) or formed by other means as would be apparent to one of ordinary skill in the art.

It is further desirable to have structural reinforcement at the side margins (112) to minimize or eliminate the possibility of the coupling member (104) from tearing the restraining member (102) when under load. Reinforced side margins may be formed by folding a portion of the restraining member (102) over a reinforcement member (122), such as a small diameter suture, which may be heat bonded between the two layers of sheet material. With this construction, a relatively low profile bead of material along the side margins (112) prevents or minimizes the possibility of tear propagation and, thus, accidental uncoupling of the restraining member (102). The small diameter suture (122) may comprise ePTFE, for example.

As the restraining member (102) constrains a collapsed self-expanding stent-graft, for example, forces resulting from stored spring energy in the collapsed stent-graft (106) will be acting on the restraining member (102) when it is configured for delivery. Thus, the restraining member (102) may comprise a material which is creep resistant and can withstand required loads without stretching over time. The restraining member (102) may comprise, for example, ePTFE, which is believed to provide suitable creep resistance, flexibility, and biocompatibility in a thin sheet form which can be heat bonded. Other materials also may be used including polyethers such as polyethylene terepthalate (DACRON® or MYLAR®) or polyaramids such as KEVLAR®.

The thread-like coupling member (104) may also comprise ePTFE. Sutures of polyethers such as polyethylene terepthalate (DACRON® or MYLAR®) or polyaramids such as KEVLAR® or metal wire comprising nitinol, stainless steel or gold may also be used for the coupling member (104). The coupling member (104) may simply extend to form a remote pull line as will be discussed below. Alternatively, a metallic pull line, such as one comprising stainless steel may be coupled to a nonmetallic coupling member (104) such as one comprising ePTFE. The coupling may be made by folding the end of the metallic pull line back upon itself to form an eyelet and threading the coupling member therethrough and securing it to the eyelet with a knot.

It is further noted that the width of the restraining member, when in a flat orientation as shown in FIG. 7A preferably, is less than the diameter of the implant. Typically the restraining member width will be less than about 40 mm (typically about 25–40 mm when the device is sized for thoracic aorta applications), and more typically less than about 15 mm. The sheet of material preferably has a thickness less than 0.010 inch (0.254 mm) and more preferably less than 0.005 inch (0.127 mm). In addition, the length of the restraining member preferably is less than or equal to that of the implant.

A retraction assembly may be provided to retract the restraining member during expansion of the implant, so that the length of the restraining member is maintained to be about equal to or less than that of the implant. The expandable portion of the implant may undergo minor amounts of shortening along the axial direction due to the expansion thereof in the radial direction, which may lead to an overlap of the restraining member at the ends of the implant, but for the use of some type of retraction assembly in these situations. The retraction assembly minimizes or eliminates the risk of the restraining member extending beyond the implant and interfering with any channel formed by the implant, or any fluid flowing therethrough after expansion.

Figure 8A:
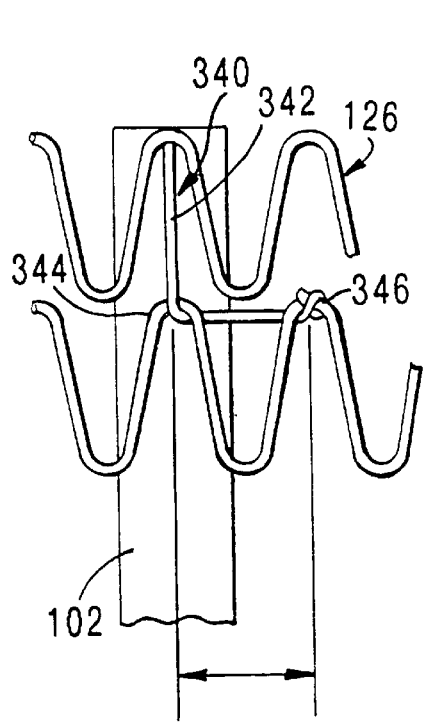
FIG. 8A shows a restraining member retraction mechanism where the mechanism is in an unactuated state.

Referring to FIGS. 8A–8D, illustrative retraction assemblies or mechanisms are shown. In FIG. 8A, a retraction assembly (340) includes a biocompatible filament (342) which includes a portion that is tied or otherwise fixed, as shown at an attachment point (348), adjacent to the end of the restraining member (102). Filament (342) is passed underneath the members forming the first or end helical turn of the stent (126) and looped under or otherwise slidably secured to a portion of the second, third or another helical turn other than the first helical turn such as an apex (344) in a second turn. The other end portion of filament (342) is further fixed, by tying or some alternative to tying, to a portion of the stent that is circumferentially spaced from the attachment point (348) or apex (344), for example, such as an apex (346) of the same helical turn. Preferably, the filament (342) is looped through an apex of the second helical turn and tied to an apex (346) which is adjacent to the looped apex (344) as shown in FIG. 8A.

Figure 8B:
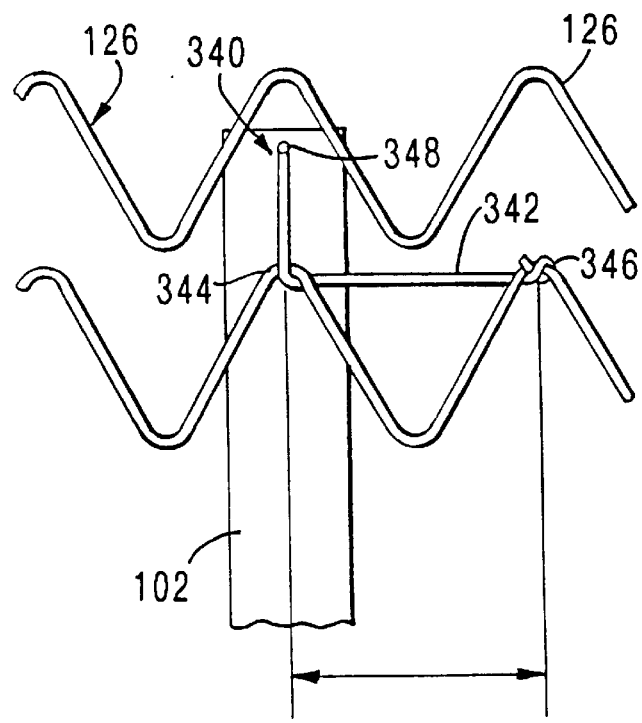
FIG. 8B shows the mechanism of FIG. 8A in an actuated state.

FIG. 8A shows the stent in a compressed state. Upon expansion of the stent, as mentioned above, the members of the stent expand to effect the radial expansion of the stent, as shown in FIG. 8B. Because the distance between apexes (344) and (346) becomes greater upon expansion of the stent, and because the filament (342) is relatively unyieldable and inelastic, the distance between the attachment point (344) and the apex (348) necessarily decreases. The result is that the end of the restraining member (102) is retracted with respect to the stent (126), as shown in FIG. 8B. Thus, the retraction along the longitudinal axis of the restraining member is driven by the expanding distance between adjacent apexes in this variation. Although only one retraction mechanism is shown, another similarly configured and arranged retraction mechanism may be used at the other end of the restraining member.

Figure 8C:
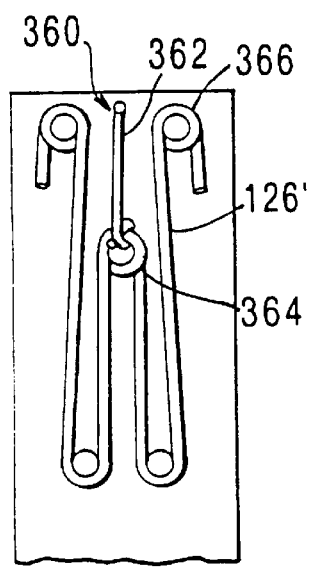
FIG. 8C shows a retraining member retraction mechanism according to yet another variation where the mechanism is in an unactuated state.
Figure 8D:
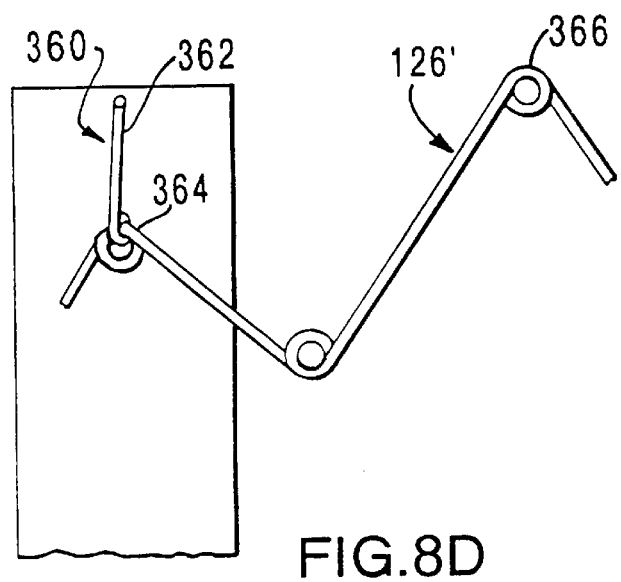
FIG. 8D shows the mechanism of FIG. 8C in an actuated state.

FIG. 8C shows another variation for a retraction assembly. The view of this assembly as that shown in FIGS. 8A and 8B are taken from a location between the generally cylindrical graft and stent looking radially outward. In contrast to that shown above where one end portion of a filament is secured to the restraining member and another to a portion of the stent that circumferentially moves during stent expansion, the other end of the filament is secured to a portion of a stent that moves generally parallel to the longitudinal axis of the stent (axially) as the stent expands. In this variation, at least one apex (364) of an end helix of the stent member (126') (which differs from stent (126) in that it includes eyelets which may be formed as shown in the drawings) is made shorter than the majority of apexes (366). A filament (362) is tied or otherwise fixed at one end to apex (364), and at the other end, to one end portion of the restraining member (102). As shown in FIG. 8D, upon radial expansion of the stent, inwardly positioned apex (364) retracts to a greater extent in the longitudinal or axial direction than the full height apexes (366). This relative greater retraction directly translates through filament (362) such that the end of the restraining member (102) is retracted relative to apexes (366). As described above, another similarly constructed retraction mechanism may be provided at the other end of the restraining member.

Returning to FIG. 6, one stent-graft construction that may be used in conjunction with the delivery systems disclosed herein is shown. Stent-graft (106) generally includes a thin-walled tube or graft member (124), a stent member (126), which can be a self-expanding stent, and a ribbon or tape member (128) for coupling the stent (126) and graft (124) members together. The stent (126) and graft (124) members may be heat bonded together, thus scaling in portions of the stent member (126) that are between the tape member (128) and the graft member (124). The mechanical properties of the stent-graft (128) may be customized, for example, through materials selection, by varying the structural pattern of the stent member, varying the thickness of the tape (128) and graft (124) members, and varying the pattern with which the tape member contacts the stent and graft members.

As shown in FIG. 6A, the tape member (128) may cover only a portion of the stent member (126) as it follows the helical turns of the undulating stent member. With this construction, regions of the stent member do not interface with the tape member when the stent-graft is in an uncompressed state, for example. This is believed to advantageously reduce shear stresses between the stent member (126) and the tape member (128) when the stent-graft undergoes bending or compression, thereby reducing the risk of tearing the graft (124) or tape (128) members or causing delamination between the stent (125) and graft (124) members.

The tape member (128) also preferably has a generally broad or flat surface for interfacing with the stent (126) and graft (124) members as compared to filament or thread-like structures such as sutures. This increases potential bonding surface area between the tape member (128) and the graft member (124) to enhance the structural integrity of the stent-graft. The increased bonding surface area also facilitates minimizing the thickness of the tape member (128). It has been found that a tape member in the form of a generally flat ribbon as shown in the drawings provides desired results.

Tape members having widths of 0.025, 0.050 and 0.075 inches applied to a stent member having a peak-to-peak undulation amplitude of about 0.075 inch are believed to provide suitable results. However, it has been found that as the tape member band width increases, the stent-graft flexibility generally is diminished. It is believed that a tape member width of about one-fourth to three-fourths the amplitude of the stent member undulations, measured peak-to-peak, may be preferred (may be more preferably about one-third to two-thirds that amplitude) to optimize flexibility. It also has been found that by positioning one of the lateral margins of the tape member adjacent to the apexes, the tape member width may be reduced without significantly sacrificing apex securement. Varying the width of the tape member (e.g., varying width of the tape along the length of the stent graft) can also result in the adjustment of other structural properties. Increasing the width can also potentially increase the radial stiffness and the burst pressure and decrease the porosity of the device. Increasing band width can also diminish graft member wrinkling between coupling member turns.

The tape member (or separate pieces thereof) also may surround the terminal end portions of the stent-graft to secure the terminal portions of the graft member to the stent member.

Figure 9A:
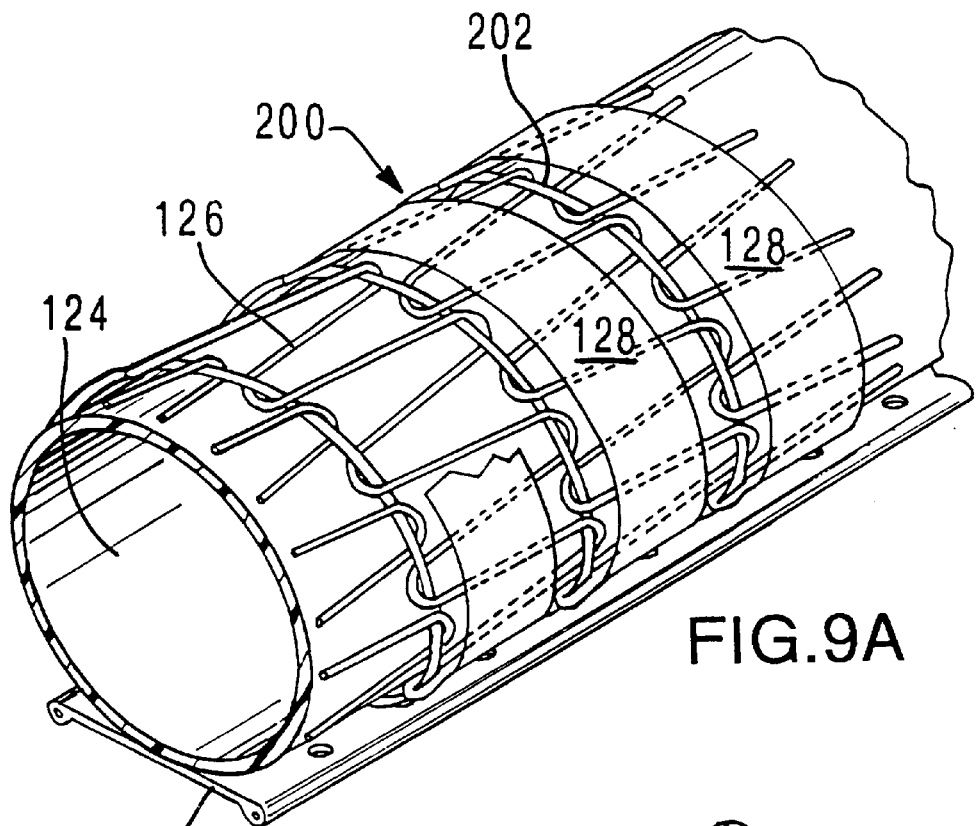
FIG. 9A is a perspective view of another variation of the implant in conjunction with the restraining member of FIG. 4.
Figure 9B:
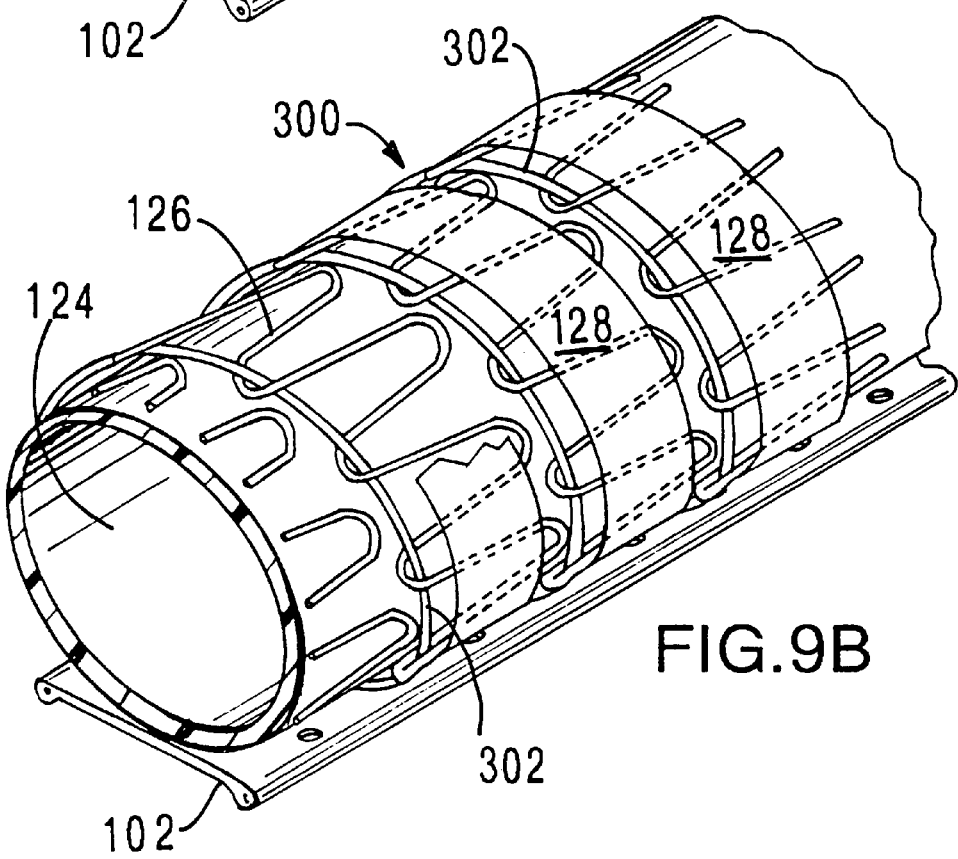
FIG. 9B is a perspective view of a further variation of the implant in conjunction with the restraining member of FIG. 4.

FIGS. 9A and 9B illustrate further stent-graft constructions that may be used with the delivery systems described herein. Referring to FIG. 9A, stent-graft (200) is the same as stent-graft (106) with the exception that stent-graft (200) includes a filament that couples stent undulations in adjacent turns. Filament (202) is laced or interwoven between undulations of the stent member and acquires a helical configuration (i.e., it forms a secondary helix) in being laced as such. Such a configuration is disclosed in PCT publication No. WO 95/26695 (International Application No. PCT/US95/04000) the entirety of which is hereby incorporated herein by reference. The stent-graft (300) shown in FIG. 9B is the same as that shown in FIG. 9A with the exception that the filament (302) is interwoven between undulations in the same helical turn of the stent member.

The filaments (202, 302) are of the same construction and may be of any appropriate filamentary material which is blood compatible or biocompatible and sufficiently flexible to allow the stent to flex and not deform the stent upon folding. Although the linkage may be a single or multiple strand wire (platinum, platinum/tungsten, gold, palladium, tantalum, stainless steel, etc.), much preferred is the use of polymeric biocompatible filaments. The flexible link may be tied-off at either end of the stent-graft (100), for example, by wrapping its end portion around the stent and tying it off at the point at the beginning of the last turn as would be apparent to one of ordinary skill.

A percutaneously delivered stent-graft must expand from a reduced diameter, necessary for delivery, to a larger deployed diameter. The diameters of these devices obviously vary with the size of the body lumen into which they are placed. For instance, the stents of this invention may range in size from 2.0 mm in diameter (for neurological applications) to 40 mm in diameter (for placement in the aorta). A range of about 2.0 mm to 6.5 mm (perhaps to 10.0 mm) is believed to be desirable. Typically, expansion ratios of 2:1 or more are required. These stents are capable of expansion ratios of up to 5:1 for larger diameter stents. Typical expansion ratios for use with the stents-grafts of the invention typically are in the range of about 2:1 to about 4:1 although the invention is not so limited. The thickness of the stent materials obviously varies with the size (or diameter) of the stent and the ultimate required yield strength of the folded stent. These values are further dependent upon the selected materials of construction. Wire used in these variations are typically of stronger alloys, e.g., nitinol and stronger spring stainless steels, and have diameters of about 0.002 inches to 0.005 inches. For the larger stents, the appropriate diameter for the stent wire may be somewhat larger, e.g., 0.005 to 0.020 inches. For flat stock metallic stents, thicknesses of about 0.002 inches to 0.005 inches is usually sufficient. For the larger stents, the appropriate thickness for the stent flat stock may be somewhat thicker, e.g., 0.005 to 0.020 inches.

The following example is provided for purposes of illustrating a preferred method of manufacturing a stent-graft as shown in FIG. 6. It should be noted, however, that this example is not intended to limit the invention. The stent member wire is helically wound around a mandrel having pins positioned thereon so that the helical structure and undulations can be formed simultaneously. While still on the mandrel, the stent member is heated to about 460° F. for about 20 minutes so that it retains its shape. Wire sizes and materials may vary widely depending on the application. The following is an example construction for a stent-graft designed to accommodate a 6 mm diameter vessel lumen. The stent member comprises a nitinol wire (50.8 atomic % Ni) having a diameter of about 0.007 inch. In this example case, the wire is formed to have sinusoidal undulations, each having an amplitude measured peak-to-peak of about 0.100 inch and the helix is formed with a pitch of about 10 windings per inch. The inner diameter of the helix (when unconstrained) is about 6.8 mm. (The filament when used as shown in FIGS. 9A and 9B may have a diameter of about 0.006 inch.)

In this example, the graft member is porous expanded polytetrafluoroethylene (PTFE), while the tape member is expanded PTFE coated with FEP. The tape member is in the form of a flat ribbon (as shown in the illustrative variations) that is positioned around the stent and graft member as shown in FIG. 6. The side of the tape member or ribbon that is FEP coated faces the graft member to secure it to the graft member. The intermediate stent-graft construction is heated to allow the materials of the tape and graft member to merge and self-bind as will be described in more detail below.

The FEP-coated porous expanded PTFE film used to form the tape member preferably is made by a process which comprises the steps of:

(a) contacting a porous PTFE film with another layer which is preferably a film of FEP or alternatively of another thermoplastic polymer;

(b) heating the composition obtained in step (a) to a temperature above the melting point of the thermoplastic polymer;

(c) stretching the heated composition of step (b) while maintaining the temperature above the melting point of the thermoplastic polymer; and (d) cooling the product of step (c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

In constructing this example, the thin wall expanded PTFE graft was of about 0.1 mm (0.004 in) thickness and had a density of about 0.5 g/cc. The microstructure of the porous expanded PTFE contained fibrils of about 25 micron length. A 3 cm length of this graft material was placed on a mandrel the same diameter as the inner diameter of the graft. The nitinol stent member having about a 3 cm length was then carefully fitted over the center of the thin wall graft.

The stent-member was then provided with a tape coupling member comprised of the FEP coated film as described above. The tape member was helically wrapped around the exterior surface of the stent-member as shown in FIG. 6. The tape member was oriented so that its FEP-coated side faced inward and contacted the exterior surface of the stent-member. This tape surface was exposed to the outward facing surface of the thin wall graft member exposed through the openings in the stent member. The uniaxially-oriented fibrils of the microstructure of the helically-wrapped ribbon were helically-oriented about the exterior stent surface.

The mandrel assembly was placed into an oven set at 315° C. for a period of 15 minutes after which the film-wrapped mandrel was removed from the oven and allowed to cool. Following cooling to approximately ambient temperature, the mandrel was removed from the resultant stent-graft. The amount of heat applied was adequate to melt the FEP-coating on the porous expanded PTFE film and thereby cause the graft and coupling members to adhere to each other. Thus, the graft member was adhesively bonded to the inner surface of the helically-wrapped tape member through the openings between the adjacent wires of the stent member. The combined thickness of the luminal and exterior coverings (graft and tape members) and the stent member was about 0.4 mm.

Although the invention has been described with reference to the stent-graft examples illustrated in the drawings, it should be understood that it can be used in conjunction with other devices, stents or stent-grafts having constructions different than those shown. For example, delivery systems described herein may be used in conjunction with bifurcated stents or stent-grafts as will be described in detail below. In addition, although a self-expanding stent-graft has been described, balloon expanding stent-grafts also may be used in conjunction with the delivery systems described herein. These stent-grafts require a balloon to expand them into their expanded state as opposed to the spring energy stored in a collapsed self-expanding stent.

Figure 10A:
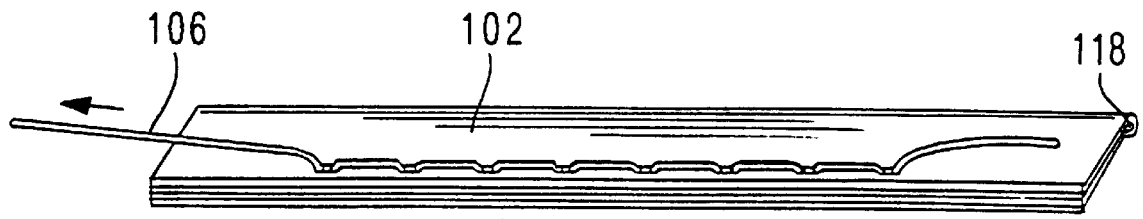
FIG. 10A illustrates the restraining and coupling member of FIG. 4 and the pull direction for removing the coupling member from the restraining member.
Figure 10B:
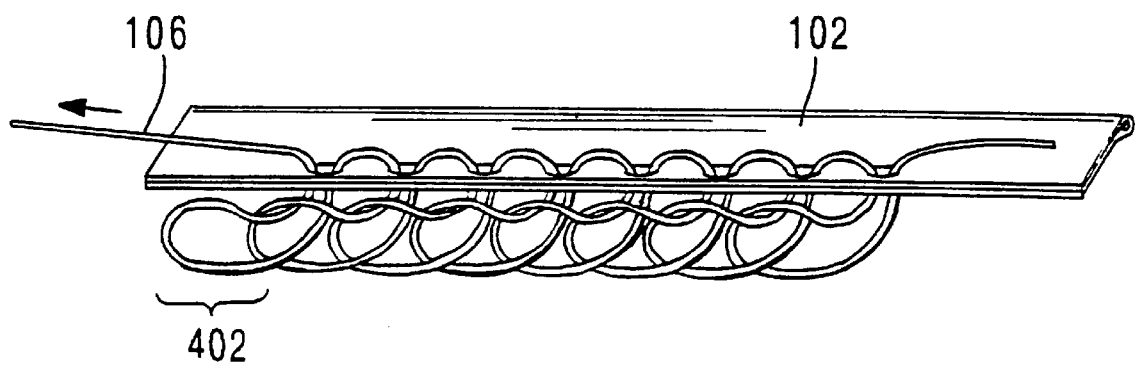
FIG. 10B shows the assembly of FIG. 10A with the coupling member loosened to illustrate the chain knots used according to one variation.
Figure 10C:
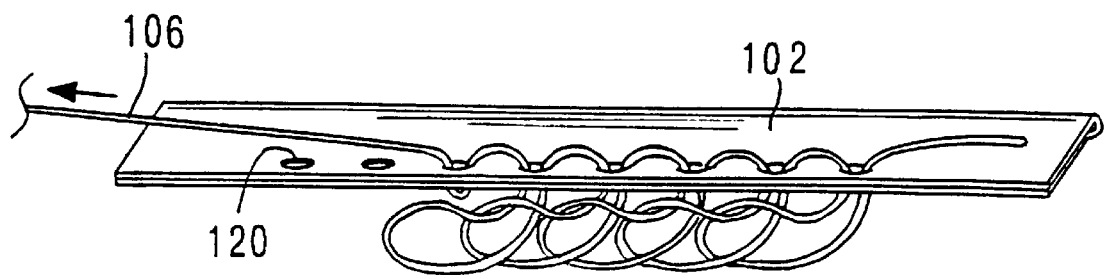
FIG. 10C diagrammatically represents release of the assembly of FIG. 10A or 10B as the coupling member is pulled in the direction shown.

Referring to FIGS. 10A–C, one slip knot configuration that may be used in conjunction with the thread-like coupling member (104) will be described. The restraining member (102) is shown without an implant positioned therein for purposes of simplification. FIG. 10A illustrates the slip knot in a prerelease or predeployment state, the series of knots are generally flush with the restraining member (102) surface and add very little profile to the construct which is preferred during implant delivery. FIG. 10B shows the assembly of FIG. 10A with the thread-like coupling member (104) loosened to illustrate how the chain knots (130) may be formed. FIG. 10C diagrammatically represents release of the assembly of FIGS. 10A or 10B. The illustrated stitches or knots is releasable by pulling one end of the line that results in releasing of the cylindrical or tubular restraining member and then deployment of the device. This particular stitch is called a "chain stitch" and may be created with a single needle and a single line. A chain stitch is a series of loops or slip knots that are looped through one another such that one slip knot prevents the next slip knot from releasing. When the line is pulled to release a slip knot, the following slip knot is then released and that releases the next slip knot. This process continues during pulling of the line until the entire line is pulled out of the restraining member.

Referring to the drawings, as the unknotted portion or the lead (132) of the thread-like coupling member (104) is pulled, such as in the direction shown by reference arrow (134), each consecutive chain knot (130) releases the next adjacent one. In the preferred embodiment, the chain knots (130) of the coupling member (104) are arranged to progressively release the collapsed implant in a direction away from the distal portion of the delivery catheter as shown in FIG. 10A and as will be discussed in detail below.

Figure 11D:
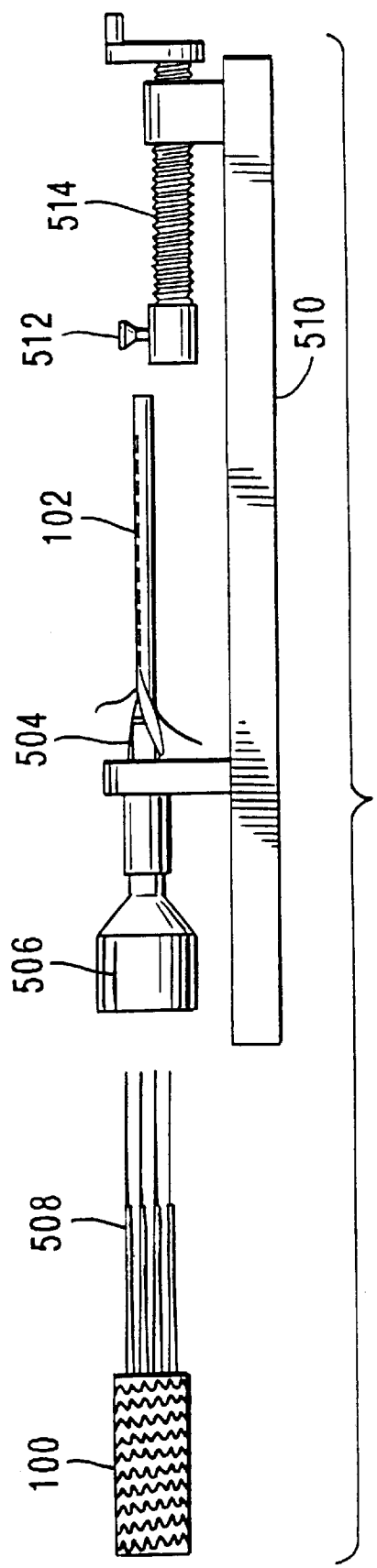
Figure 11E:
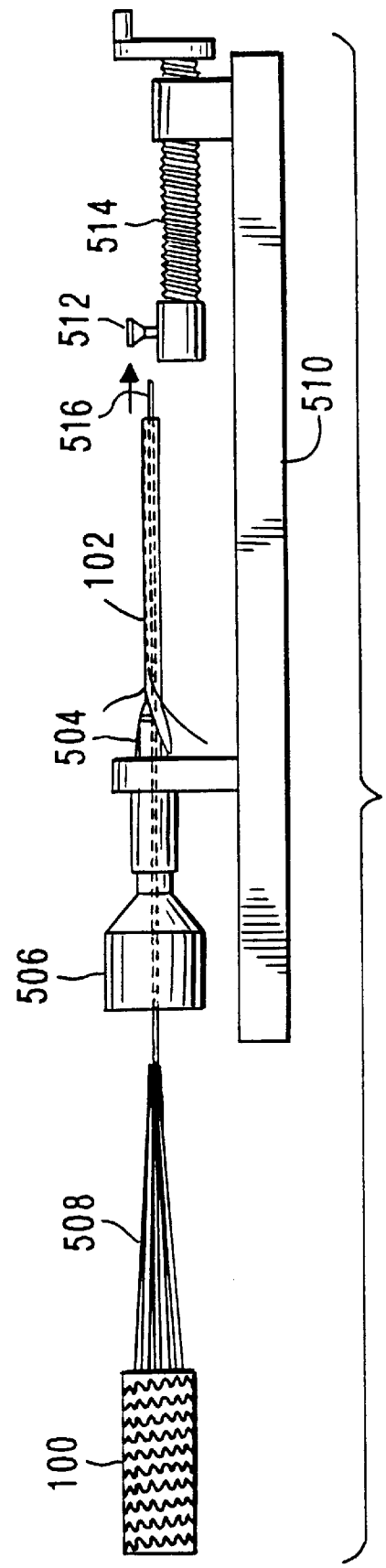
Figure 11F:
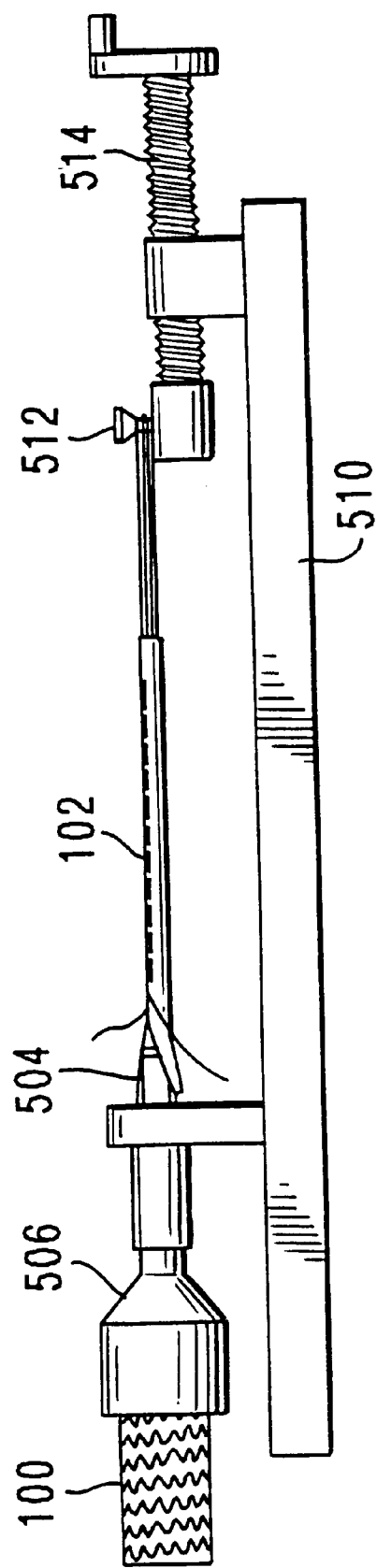

Referring to FIGS. 11A through 11F, a method for making an assembly comprising a restraining member with a collapsed or compressed implant therein is shown for purposes of example. FIG. 11A shows the restraining member (102) with its side margins releasably coupled to one another and its left end dilated by a tapered mechanical dilator (402). A small funnel (404) is then inserted into the restraining member (102) as shown in FIGS. 11B and 11C. The small funnel (404) and restraining member (102) are then mounted onto a pulling frame (410), and a large funnel (406) is fitted into the small funnel (404) as shown in FIG. 11D. Traction or pull lines (408), which have been sutured to one end of the stent-graft, (106) are pulled through the large funnel (406), small funnel (404), and restraining member (102) with a tapered mandrel (416). As shown in FIG. 11F, the pull lines (408) are fastened to a tie down post (412) located on a tension screw (414) and then are pulled by the tension screw (414). The stent-graft (106) is then pulled and collapsed sequentially through the large (406) and small (404) funnels, and then into the restraining member (102). Once the stent-graft (106) has been radially collapsed into the restraining member (102), which has its side margins coupled together, the pull lines (408) can be removed. The mandrel (416) may be inserted into the restrained implant to facilitate introduction of another component. In the preferred embodiment, a multilumen catheter (136) (FIGS. 12–14) is introduced through the center of the compressed stent-graft (106) and is used to deliver the radially restrained stent-graft to the desired endolumenal site.

It also is noted that the funnels may be chilled to facilitate compression of the stent when the stent is made of nitinol. That is, when the stent is made of nitinol, the funnels may be chilled below 0° C. or below the transition temperature (Mf) where nitinol is in its martensitic state. In addition, the stent-graft could be folded first and then reduced in profile by pulling through the funnel and into the restraining member. Cooling may be accomplished by spray soaking the stent-graft with chilled gas such as tetrafluoroethane. Micro-Dust™ dry circuit duster manufactured by MicroCare Corporation (Connecticut) provides suitable results. The spray canister preferably is held upside down to discharge the fluid as a liquid onto the stent-graft.

A method of deploying an implant will be described with reference to FIGS. 12–14. In general, an implant may be delivered percutaneously with the delivery systems described herein, typically through the vasculature, after having been assembled in the reduced diameter form (see e.g. FIG. 4). At the desired delivery site, the implant may be released from the restraining member, thus allowing the implant to expand or be expanded against the lumen wall at the delivery site. Although other devices including stents or stent-grafts may be used, such as balloon expandable stents, the following example will be made with reference to a self-expanding stent-graft, which has the ability to fully expand itself into its final predetermined geometry when unconstrained. More particularly, the following example will be made using a delivery system as shown in FIGS. 4 and 10A–C and a stent-graft construction as shown in FIG. 6.

Referring to FIGS. 12A and 12B, an implant delivery assembly including a collapsed stent-graft (106) that is confined within a restraining member (102) and, which surrounds a distal portion of the delivery catheter (136), is shown. The attending physician will select a device having an appropriate size. Typically, the stent-graft will be selected to have an expanded diameter of up to about 20% greater than the diameter of the lumen at the desired deployment site.

The delivery catheter preferably is a multilumen catheter. The proximal portion of the catheter (136) is coupled to a hub (140), which includes a guidewire port (143) for a guidewire (142), and a deployment knob (144), which is coupled to the lead (132) of the thread-like coupling member (104). Accordingly, when the knob (144) is retracted, the restraining member (102) is released so that the stent-graft may expand. The hub (140) also may include a flushing port (146) as is conventional in the art. The stent-graft (106) is held axially in place prior to deployment by a proximal barrier (148) and distal barrier (150) which are positioned around delivery catheter (136) adjacent to the proximal and distal portions, respectively, of the restrained stent-graft. The proximal and distal barriers (148, 150) may be fixedly secured to the multilumen catheter (136) to restrict any axial movement of the restrained stent-graft. The barriers preferably are positioned to abut against the stent-graft or restraining member. The lead (132) of the coupling member (104) is passed through an aperture (152) in the proximal barrier (148) which is fluidly coupled to a lumen in the delivery catheter (136) so that the coupling member lead (132) can be coupled to the deployment knob (144). FIGS. 12A and 12B show advancement of the catheter (136) and the restrained implant through a vessel (154) toward a desired site.

Referring to FIGS. 13A and 13B, once the restrained stent-graft reaches the desired site (156), the deployment knob (144) is retracted so that the stent-graft progressively expands as shown in the drawings as the coupling member (104) is removed from the restraining member. The coupling member preferably is arranged to facilitate stent-graft expansion in a direction from the distal to proximal ends of the stent-graft (i.e., in a direction from the catheter tip to the catheter hub).

FIGS. 14A and 14B show the stent-graft (106) and restraining member (102) in their final implantation position after the coupling member and catheter have been removed therefrom. In another variation, multiple restraining members may be used as shown in FIG. 12C. When the multiple coupling members (104) are released simultaneously implant deployment time may be reduced.

A method for deploying a balloon expandable stent-graft may be the same as that described above, with the exception that after the coupling member (104) has been retracted from the eyelets (116), the balloon, which may be positioned inside the stent-graft prior to delivery, is inflated to expand the stent-graft (106) and then deflated for removal through the catheter (136).

According to further variations, multidirectional coupling member release or multiple coupling members may be used. These configurations may facilitate more rapid deployment of the implant than when a single unidirectional coupling member is used. FIGS. 15A–15D diagrammatically show multidirectional deployment of a restrained implant according to the principles of the invention where a coupling member arrangement is provided to release the implant from its middle portion, preferably its axial center, outward toward the implant ends. Although a particular coupling member configuration is not shown in these diagrammatic representations, one suitable coupling configuration is shown in FIG. 16 where the leads (132) may be passed through the aperture (152) and coupled to the deployment knob (144) as shown in FIG. 12A and described above.

Figure 15A:
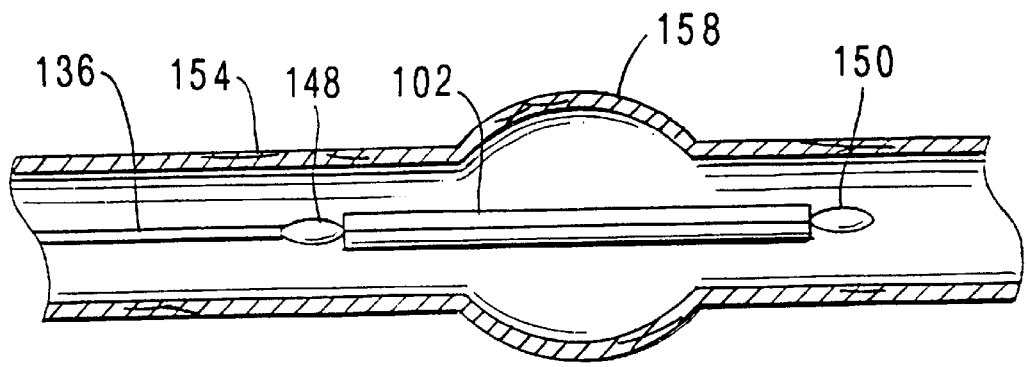
FIGS. 15A, 15B, 15C and 15D diagrammatically show deployment of a restrained implant according to another variation where the coupling member configuration provides release from the middle portion of the implant outward toward the implant ends.
Figure 15B:
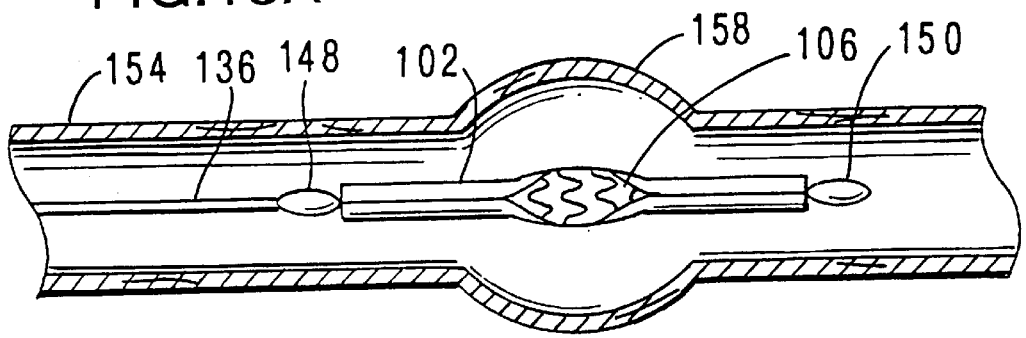
Figure 15C:
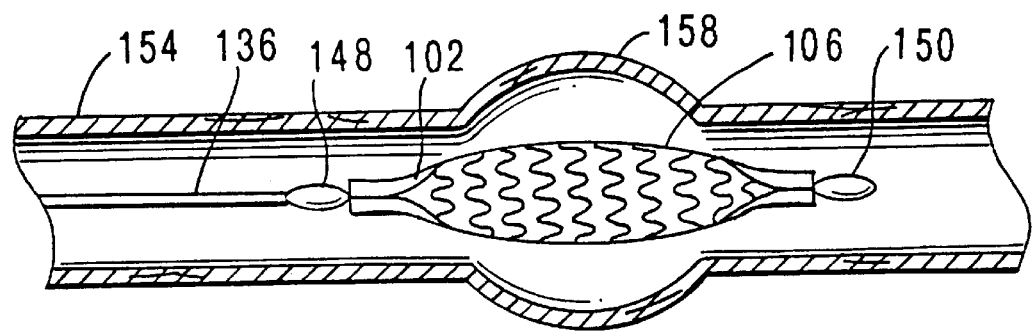
Figure 15D:
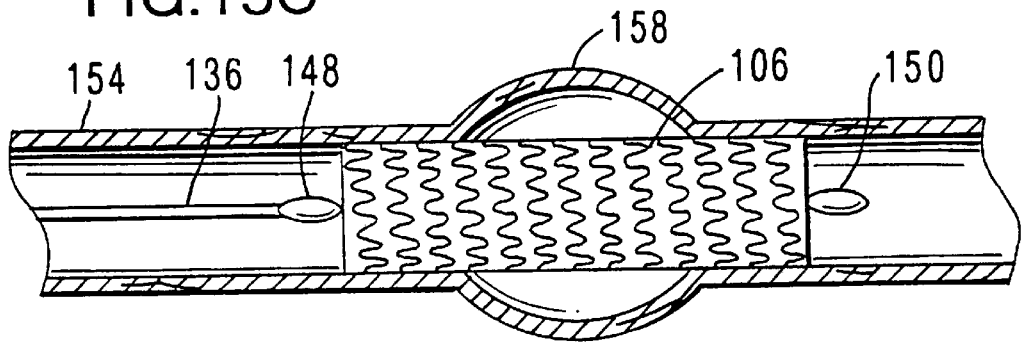

Referring to FIG. 15A, the restrained stent-graft, which is positioned on the distal end portion of delivery catheter (136), is advanced through a vessel (154) for deployment in an aneurysm (158). The axial midpoint of the restraining member (102) preferably is positioned at the center of the aneurysmal sac. As the coupling member arrangement unlacing propagates from middle of the construct toward the proximal and distal ends of the restraining member (102) and the stent-graft (106), the stent-graft (106) progressively expands from its axial midportion toward its ends as shown in FIGS. 15B and 15C. This may be accomplished by pulling the leads (132) shown in FIG. 16 simultaneously when the arrangement in that figure is used. The stent-graft size is selected so that when the restraining member is fully released and the stent-graft fully deployed as shown in FIG. 15D, the proximal and distal portions of the stent-graft are positioned against the proximal and distal necks of the aneurysm. The delivery catheter may then be retracted.

As is apparent from the drawings, this variation advantageously allows fluid flow through the aneurysmal sac to remain substantially unobstructed during the release of the restraining member. For example, the stent-graft ends are still constrained at the deployment time shown in FIG. 15C where the aneurysm neck regions are shown minimally obstructed. In addition, this simultaneous, multidirectional release of the restraining member advantageously reduces the time in which fluid flow in the vessel may disturb the implant position as it is deployed as compared to a single directional release mechanism such as that shown in FIGS. 12–14.

Figure 16:
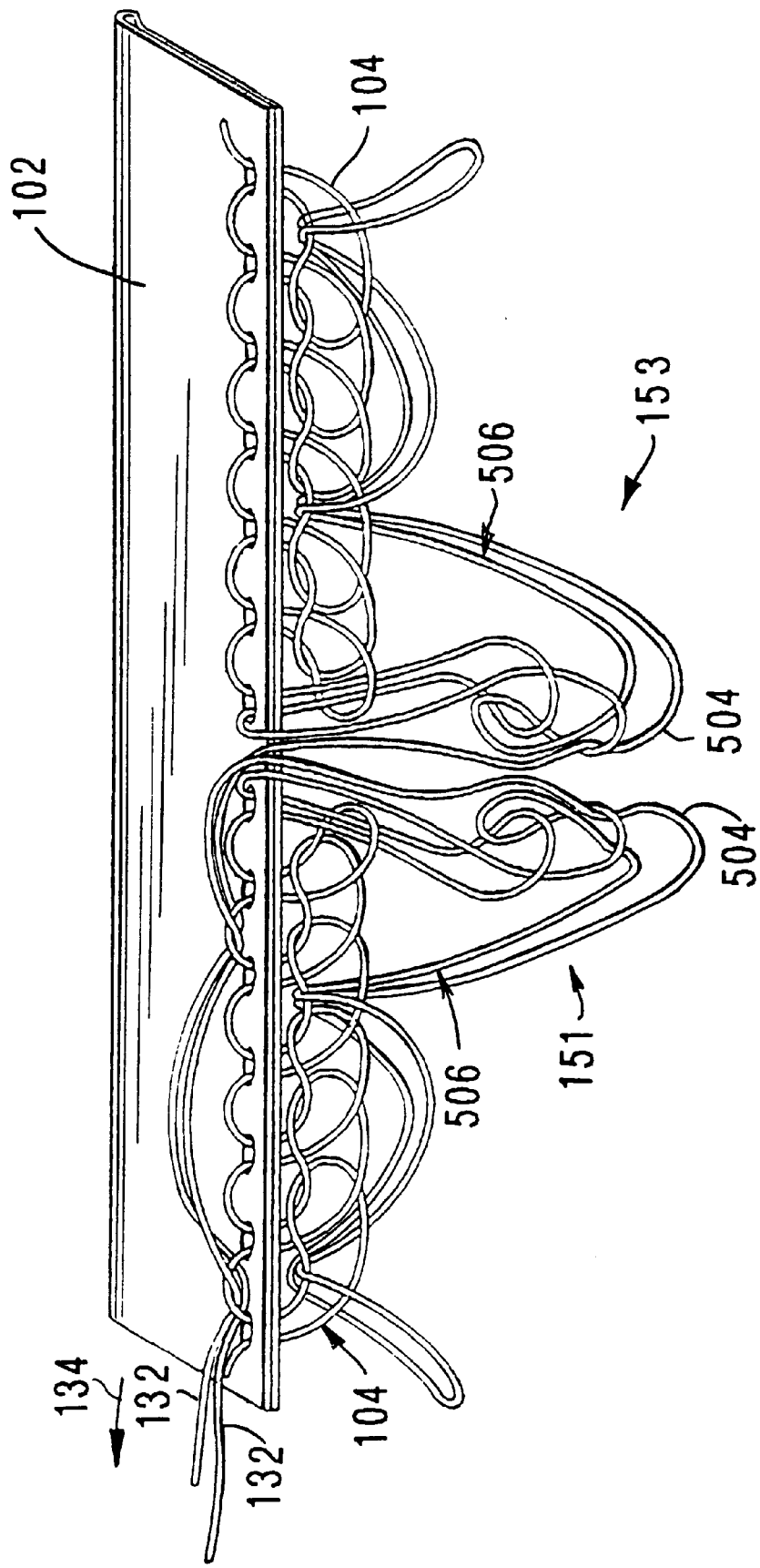
FIG. 16 illustrates one coupling member configuration for deployment as shown in FIGS. 15A–15D.

Referring to FIG. 16, a multiple coupling member configuration is shown. The illustrated arrangement includes two lacing configurations (151) and (153). Except for the placement of the lead (132) of thread-like coupling member (104) configuration (153) is the mirror image of configuration (151). Accordingly, description of only one of the configurations will be made for purposes of simplification. Referring to the lacing configuration (153), configuration (153) is the same as that shown in FIGS. 10A–C with the exception that configuration (153) further includes two additional slip knots, designated generally with reference numeral (504), and tuck arrangement (506). The additional slip knots are not interwoven in the restraining member and provide a delay mechanism for release of the coupling member, as is apparent from the drawings, when the lead (132) is pulled in the direction of the arrow (134). Thus, inadvertent pulling of the lead (132) will not immediately begin to release the coupling member from the restraining member. The tuck arrangement simply involves tucking the slack from lead (132) under stitches at various intervals as shown so that when pulled, the additional slip knots (504) may be pulled out of the way for delivery.

Bifurcated Stent or Stent-Graft

This portion of the description related to FIGS. 17A–32D generally relates to an embodiment of the current invention wherein an occlusive flange is secured as a one-way valve on an outer surface of one end portion of a self-expanding, modular, bifurcated stent-graft. The seal member is intended to prevent leakage flow around the stent-graft and into an abnormal section of vascular wall which is intended to be isolated from that flow. While much of the description related to FIGS. 17A–32D is directed toward the stent-graft structure of the tubular member, the tubular member is being so described for purposes of its role in defining this particular implantable medical device embodiment of the present invention, which is assumed to include seal member attached to the outer surface of each tubular member variation described.

This portion of the description of the invention will also use certain nomenclature which is set forth as follows. The term "distal," as hereinafter used, is meant to refer to locations that are furthest away from the surgical access point. "Proximal" is meant to refer to locations that are closer to the surgical access point. A surgical access point, for purposes of this discussion, refers to the location at which the prosthesis first enters the body, in the illustrative examples a small incision in the femoral artery. Finally, the term "prosthesis" refers to either a stent or a stent-graft. When the term stent is used, it refers to a structure that does not have a graft element whereas the term stent-graft refers to a structure that has both a stent element and a graft element.

The tubular member of this embodiment, as shown in particular forms in the FIGS. 17A–32D, is a modular prosthesis adapted for placement at a bifurcation site with the body. For illustrative purposes, this embodiment will be described with reference to the location in the human body where the abdominal aorta bifurcates into the ipsalateral and contralateral iliac arteries. It should be understood, however, that this embodiment may be used at many other locations within the body.

The stent-graft components that will be discussed below comprise a flexible graft member attached to a wire stent member using a tape member. Preferably the stent-graft components are designed for compressed delivery and are self-expanding, again as discussed in detail in reference to FIGS. 4–13 above.

Figure 17B:
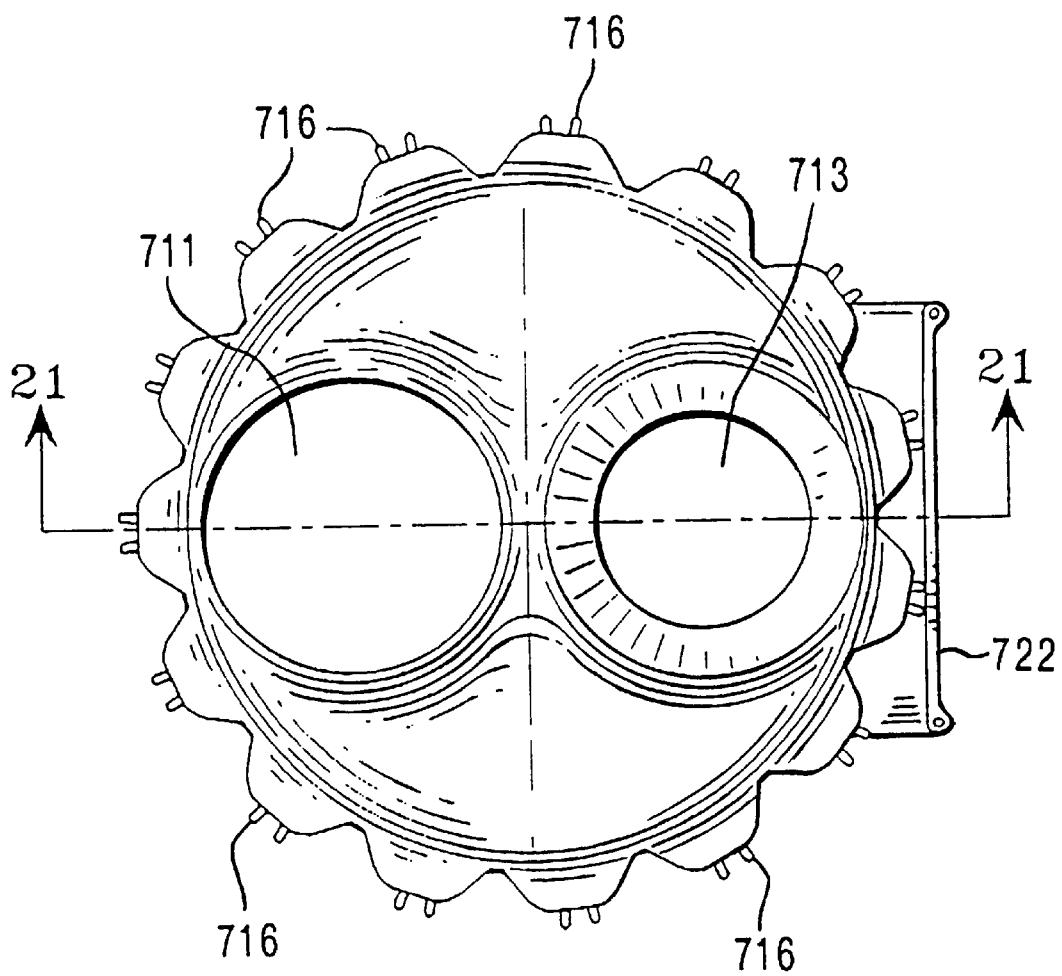
FIG. 17B is a top plan view of the bifurcated stent-graft of FIG. 17A.

The modular stent-graft of FIGS. 17A through 17b generally has two principal components; a main body (700) and a contralateral leg (730) each generally having a graft member attached to a stent member according to the description above. The main body (700) generally has a number of sections which have distinct overall constructions. A distal trunk section (708) has a single lumen structure beginning at a distal end (702) of the main body (700) and continuing until a bifurcation point (728). The bifurcation point (728) is the location within the prosthesis where the single lumen of the distal trunk section (708) bifurcates into internal two flow lumen.

An intermediate section (710) begins at the bifurcation point (728) and continues to the receiving hole (704). In the intermediate section (710), the stent-graft has an internal graft structure which is bifurcated into two lumen surrounded by a generally tubular, single-lumen stent structure. Finally, a proximal section (712) is a single lumen structure for both the stent member and the graft member and includes an ipsalateral leg (726) which terminates at an ipsalateral leg hole (706).

The graft member of the intermediate section (710) bifurcates the single lumen distal trunk section (708) into the ipsalateral leg (726) and an internal female receiving lumen (703). The receiving lumen (703) terminates at a receiving hole (704). The receiving hole (704) and receiving lumen (703) accommodate delivery and attachment of the contralateral leg component (730). Preferably, the graft material at the distal end (734) of the contralateral leg component (730) is scalloped as shown more clearly in FIG. 23 discussed below.

The receiving hole (704) is supported by a wire structure around a substantial portion of its periphery so that the receiving hole (704) is held open after deployment. In a preferred variation the wire structure that supports the receiving hole (704) is an independent wire ring (714).

The independent wire ring (714) is located in the general area of the receiving hole (704) in the intermediate section (710). The independent wire ring (714) ensures that the graft material at the receiving hole (704) is supported in an open position to receive the distal end (734) of the contralateral leg (730). In absence of such support, the receiving hole (704) may not reliably open after delivery of the main body component (700) because within the intermediate section (710) the bifurcated graft member in the area of the receiving lumen (703) does not have full stent support on its interior periphery. This may be better seen in FIG. 18 which shows the absence of any internal stent support of the interior graft periphery (785) in the area of the receiving lumen (703).

The independent wire ring (714) may be comprised of the same materials as the other stent-graft sections discussed above and is preferably self-expanding. In a preferred variation, the independent wire ring comprises a single turn of an undulating wire stent material surrounded by at least one layer of tape which is heat bonded to the receiving hole (704). Alternatively, the independent wire ring (714) could be formed as the last turn of the main body (700).

A radiopaque marker may be used to make the receiving hole (704) visible during implantation. Such a marker may include a radiopaque wire adjacent to the independent wire ring (714). Such markers make it easier to see the location of the receiving hole (704) after deployment of the main body (700) within the mammalian body.

Figure 17C:
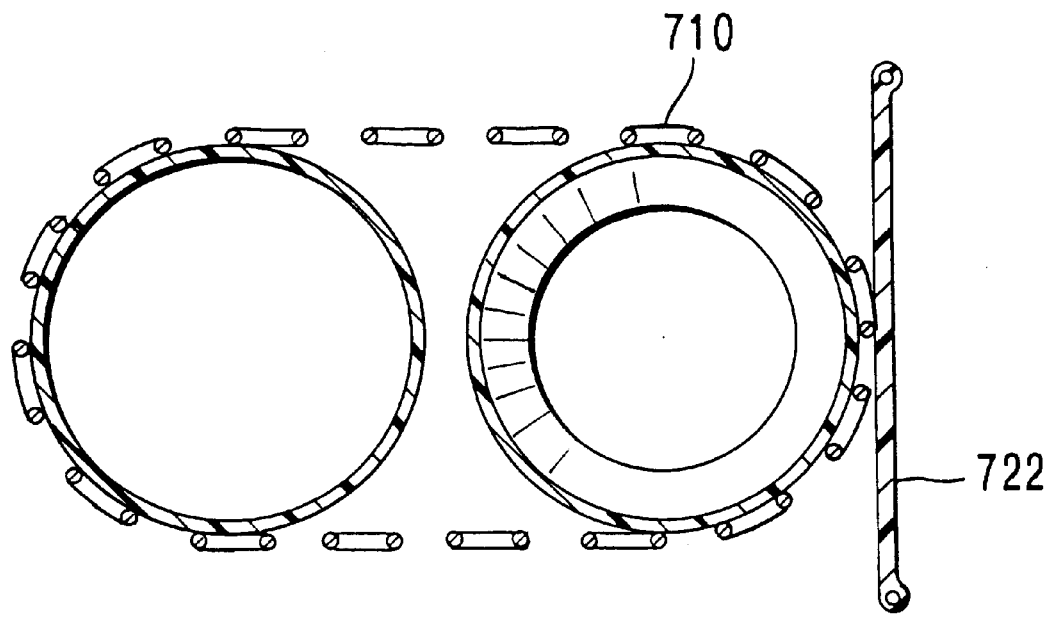
FIG. 17C is a cross-sectional view taken along section line 17C—17C depicted in FIG. 17A.

This construction of the intermediate stent section (710), as seen in cross-section in FIG. 17C, is characterized by a single-lumen stent member and bifurcated graft member and offers both a smaller compressed profile as well as simplified manufacturing over constructions which have discreet stented leg features. The compressed profile is determined largely by the physical amount of stent and graft material present in a given section. This construction eliminates the stent material that would normally support the inside periphery of the bifurcated graft section resulting in less stent material to compress in that region. As the main body component (700) is compressed for delivery as discussed above, the compressed profile is significantly smaller than would be a structure that had a section of bifurcated stent over the section of bifurcated graft.

Even though bifurcated flow is supported, manufacturing is simplified because there is no bifurcated stent section. Winding a bifurcated stent section in one piece, for example, is a more complex process. Likewise, winding separate cylindrical stent structures and connecting them to form a bifurcated stent structure is complicated and ultimately may be less reliable. The intermediate section (710) allows the entire stent member that covers the main body component (700) to be made from a single undulating wire arranged in multiple helical turns. The result is a bifurcated stent-graft device which is simple to manufacture, easily compressible and which expands reliably upon deployment.

Figure 17D:
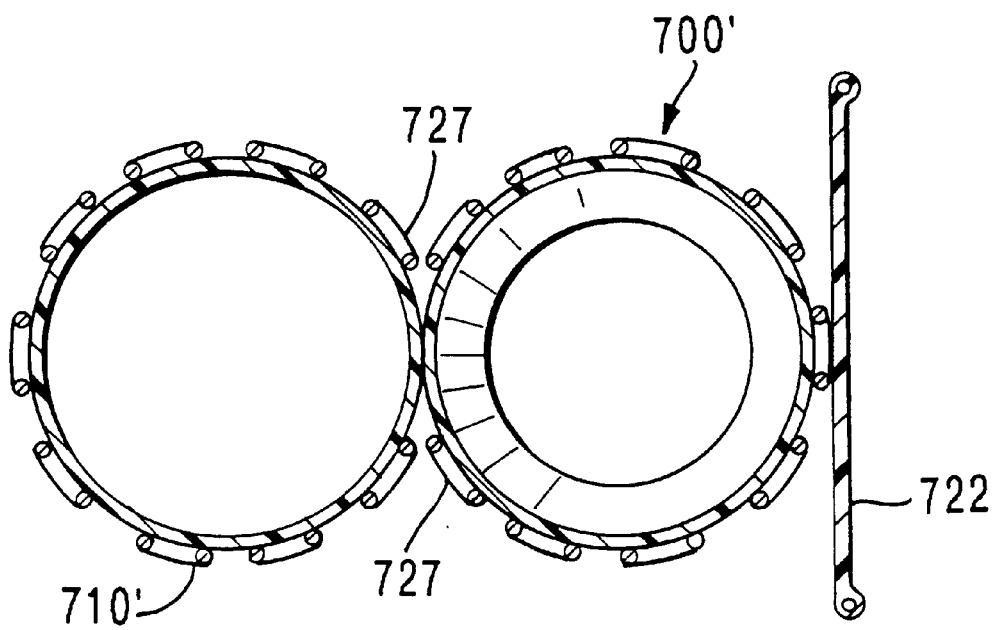
FIG. 17D is a cross-sectional view taken along section line 17D—17D depicted in FIG. 17A.

An alternative construction of the intermediate stent section (710) is shown in FIG. 17D. The intermediate stent section (710') has a shape characterized by the indented regions (727). The shape could generally be described as a 'figure-8', except that the area between the bifurcated graft member remains unsupported at its centermost region. This construction is still a single lumen stent construction and therefore maintains much of the benefits of reduced profile and simplified manufacturability while providing the bifurcated graft member with increased support around a greater portion of its perimeter. Further, indented portions (727) have less of a tendency to spring outward upon application of external forces.

As mentioned above, the main body component (700) and the contralateral leg component (730) are adapted for delivery in a compressed state to a bifurcation site within a body. For this purpose the main body component (700) is preferably equipped with a restraining member (722) constructed as described above. Likewise, the contralateral leg component (730) has an attached restraining member (732). These restraining members are typically sutured to the graft material at intervals down their length.

Figure 18:
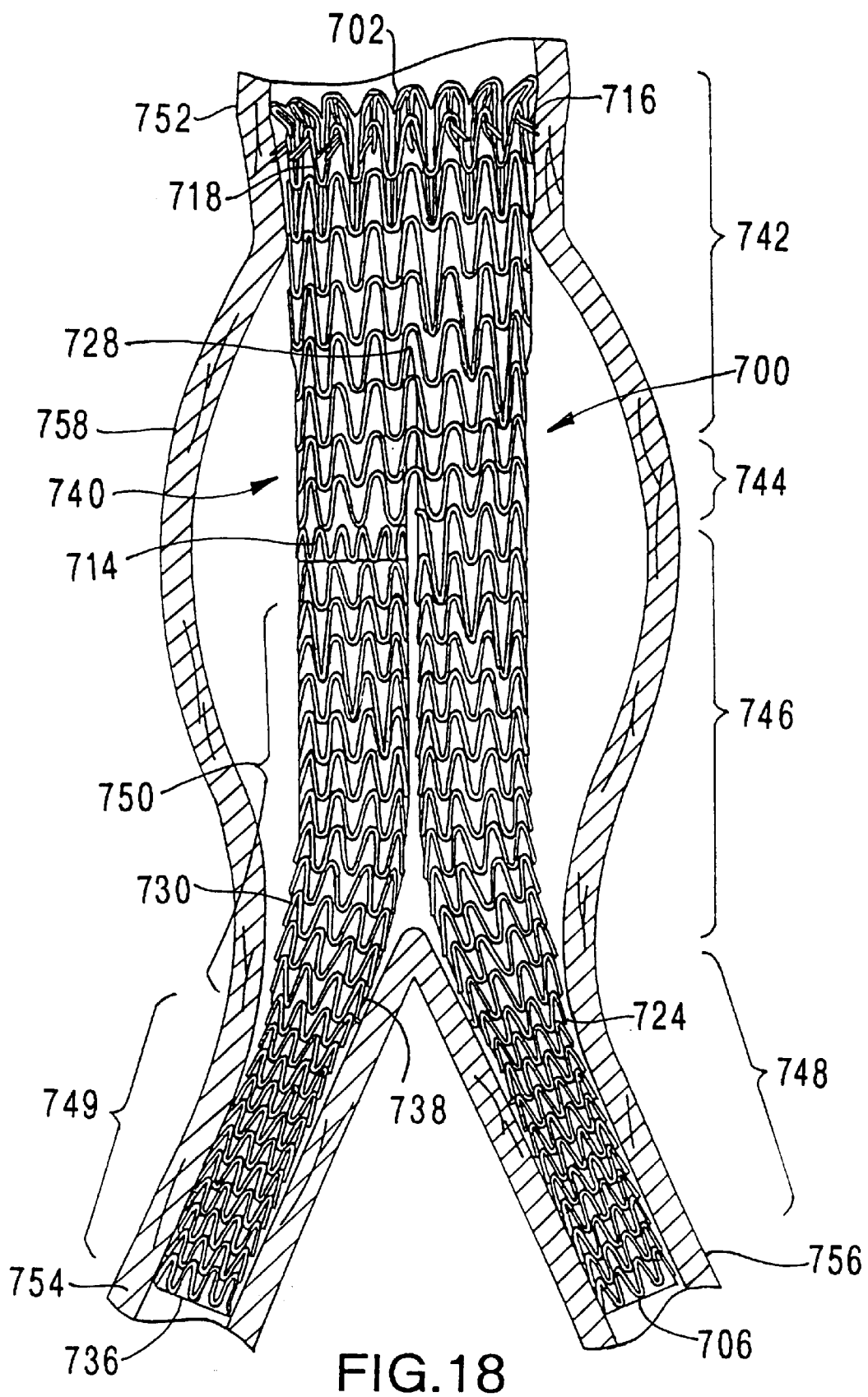
FIG. 18 is a front view of the assembled bifurcated stent-graft of FIG. 17A placed at a bifurcation site within the vasculature of a body.

FIG. 18 shows an assembled bifurcated stent-graft (740) after deployment at a bifurcation site within a bifurcated body vessel afflicted with an aneurysm (758). Although not intended to be so limited to any particular location, the inventive prosthesis is shown at the location where the abdominal aortic artery (752) bifurcates into the left iliac artery (756) and the right iliac artery (754). So that the various features of the inventive implant are more clearly shown, the restraining member is not shown in FIG. 18.

The assembled bifurcated stent-graft (740) is comprised of the main body component (700) and the contralateral leg component (730). The distal end (734) of the contralateral leg component (730) has been inserted into the receiving leg hole (704) and the female receiving lumen (703) of the main body component (700).

For best results in deploying any stent or stent-graft of these types it is essential that they have the appropriate structural properties such as axial stiffness, flexibility and kink-resistance. With complicated structures, such as those required for treating a bifurcated site, it is increasingly difficult to obtain the desired structural properties because optimizing one may negatively effect the other.

For instance, optimizing the global axial stiffness of a stent or stent-graft will necessarily make the device significantly less flexible and consequently impair its resistance to kinking and lessen its ability to conform to the natural bends and curves of the body's vasculature. Conversely a device that has high flexibility with little axial stiffness is difficult to properly deploy and does not aid in anchoring the device in the desired location.

With these constraints in mind, it has been discovered that having a bifurcated stent-graft which has segments constructed with varying structural properties offers improved deployability, is less susceptible to kinking, and favorably tends to maintain its desired position after deployment while allowing sufficient flexibility to accommodate movement by the body. The exact structural properties desired may depend on the location where the prosthesis is to be deployed.

For these reasons, it is preferable that the bifurcated stent or stent-graft be constructed with at least two segments having structural properties different from one another. For example, in FIG. 17A, a length of the distal section (708) and the intermediate section (710) may be constructed with a higher axial stiffness for improved deployment and positional stability while the proximal section (712) may be constructed to have higher flexibility to accommodate the geometry of the iliac artery.

It may be further desirable to have a number of segments that have different structural properties. Accordingly, the main body component (700) and the contralateral leg component (730) of the assembled stent-graft (740) have segments constructed with structural properties different from adjacent segments. In one preferred variation shown in FIG. 18, the main body component (700) has four different segments constructed with different structural properties. The distal segment (742) is constructed to have higher axial stiffness than the more flexible proximally adjacent segment (744). The proximal section (748) is constructed to have a higher flexibility than that of its distally adjacent segment (746). Likewise the contralateral leg component (730) has an axially stiffer distal segment (750) and a more flexible proximal segment (749).

There are a number of ways to alter the structural properties of stent or stent-graft components. One way of selectively altering the structural properties of a stent-graft segment is to use a tape member for that segment that has different physical dimensions. Such a tape member is discussed above with reference to the tape member (128) of FIG. 4. For example the tape member width, thickness or spacing may be increased, from the preferred dimensions discussed above, in a segment where it is desirable to have increased or decreased stiffness. For example, the use of wider tape wound with closer spacing will increase the stiffness in that area.

Another way of selectively altering the structural properties of a stent or stent-graft segment is shown in FIGS. 17A and 18. Extended struts (718) and (719) may be used to increase the axial stiffness of a stent-graft segment. Extended struts are formed by extending an apex on one turn of the undulating wire until it contacts an apex on an adjacent turn. This contact between an extended strut and the apex of an adjacent stent turn provides an added amount of axial stiffness. In a preferred embodiment, a layer of tape (not shown) is applied around the device in a helical pattern that covers each of the apexes of the extended struts. This additional layer of taping keeps the strut pairs together.

Referring to FIG. 17A, a first helical stent turn (720) and a second helical stent turn (721) have a generally undulating shape having apexes. An extended strut (718) of the stent turn (720) is formed having its apex near or in contact with the apex of the stent turn (721) directly below. The extended strut (719) is similarly formed by extending an apex of the stent turn (721) directly down to contact the apex in the turn below. This pattern in continued, each time spacing the extended strut over one undulation. This results in a helical pattern of extended struts down the length of the device. Of course, the extended struts may be arranged in patterns other than the helical configuration described.

A number of these patterns may be employed in any one segment or the extended strut pattern may be used in other segments to increase axial stiffness. Preferably the distally adjacent segment (746) on the main body component (700) and the axially stiff distal segment (750) on the contralateral leg component are constructed with extended struts as shown.

Another important aspect of the present invention is achieving a secure position against the walls of the vessel lumen so that the deployed position is maintained and so that there is no leakage of luminal flow. Referring now to FIG. 15, the distal end (702) is sized to properly fit the inside diameter of the target artery, in this case the abdominal aortic artery. Typically, the prosthesis is designed to have an unconstrained diameter slightly larger than the inside of the target vessel.

The ipsalateral and contralateral legs of the assembled bifurcated stent-graft (740) are typically the same size at their distal ends regardless of the size of the distal end (702) and undergo tapered sections (724) and (738) that taper to a diameter which corresponds approximately to the internal diameter of the iliac arteries. These tapered sections (724) and (738) are preferable to abrupt changes in diameter as they tend to produce superior flow dynamics.

After deployment, the assembled bifurcated stent-graft (740) must establish sufficient contact with the healthy vessel lumen on each side of the aneurysm (758) so that the device does not migrate or dislodge when subjected to the relatively high fluid pressures and flow rates encountered in such a major artery, especially when the body again becomes mobile after recovery. Further, sufficient contact must be made so that there is no leakage at the distal end (702), the ipsalateral leg hole (706) or the proximal end (736) of the contralateral leg.

Anchoring or staying features that allow the stent or stent-graft exterior to anchor itself to the vessel lumen wall may be provided to help the device seal to the vessel wall and maintain its deployed position. For example, anchors (716) as seen in FIGS. 17A and 18 are provided on the main body component (700) and could also be provided on the contralateral leg component (730). Preferably, the top stent portion (717) is directed angularly outward. This flared stent portion works to force the anchors (716) into the vessel wall as the top stent portion (717) expands under force into radial interference with the vessel wall upon deployment.

Figure 20A:
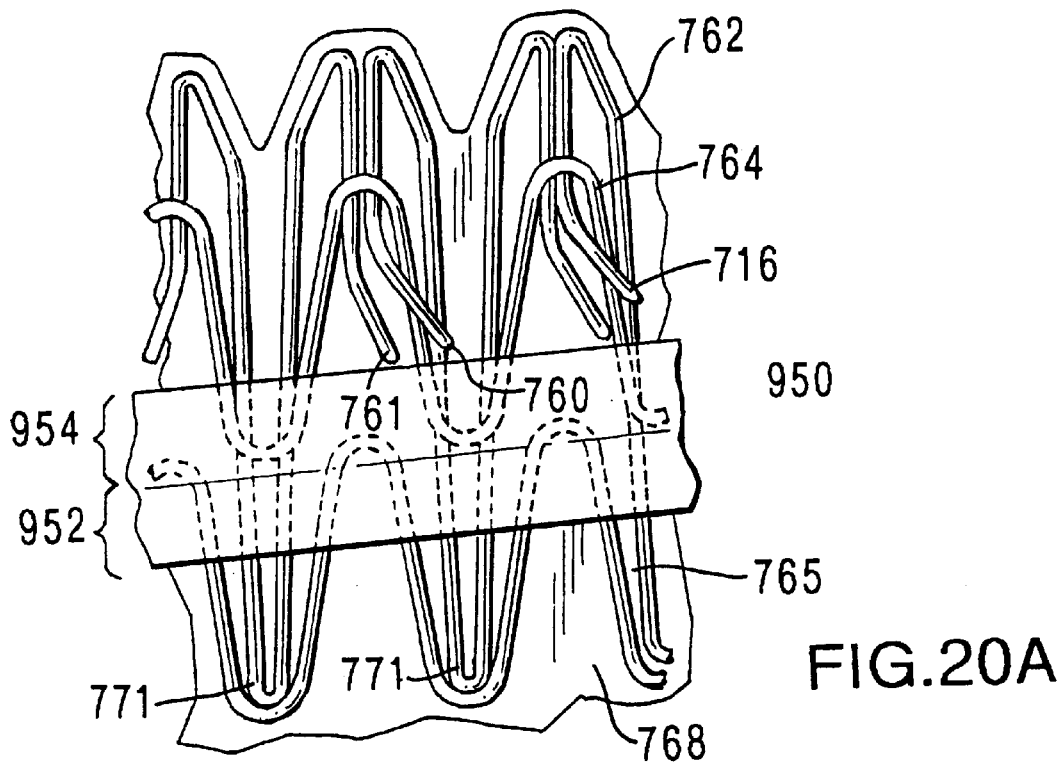
FIG. 20A is a perspective break-away view showing a close-up of a an alternative construction of the stent anchoring apexes, also including a seal member secured adjacent thereto.

A preferred construction for an anchor (716) is shown in FIG. 20A. This construction involves extending two wires from the upper stent turn (762) under an apex of an adjacent lower stent turn (764). The two ends of stent wires (760 and 761) are then bent out and away from the graft material (768). Extended struts (771) are formed adjacent to each anchor in the manner described above except the extended struts extend under the adjacent lower stent turn (764) down to a third stent turn (765). This extended strut arrangement provide, support for the anchors (716) and provides for low stresses in the wires (760 and 761) under the application of bending forces encountered as the prosthesis expands into the vessel wall. The extended struts (771) minimize the localized deformation of the stent-graft structure in the area of the anchors by providing broader support.

Figure 19:
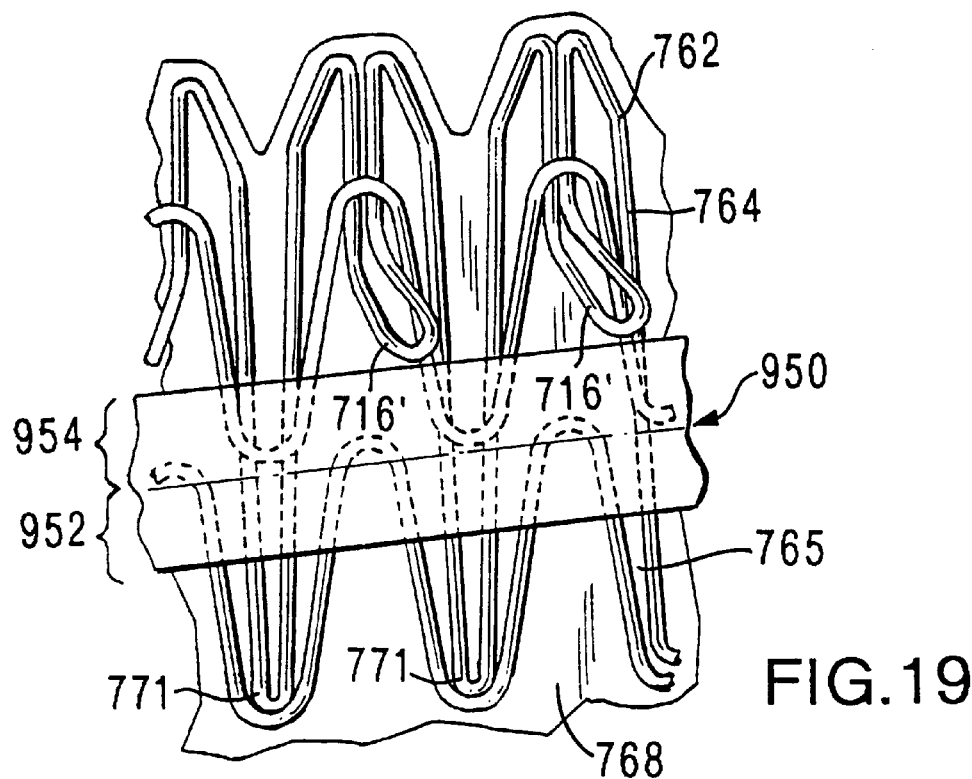
FIG. 19 is a perspective break-away view showing a close-up of one construction of the stent anchoring apexes with a seal member secured adjacent thereto.

Another construction of the anchors (716') are shown in FIG. 19. An anchor (716') is formed in the same manner except the ends of the anchor remain connected in a 'U-shape' configuration as shown. An anchor (716') may be formed at any location on the stent-graft. Most preferably, the anchors are formed in an evenly spaced pattern around the top stent portion (717) (FIG. 17A).

It should be apparent that the anchors as described above are not limited in use to the stent-graft combination shown in the figures but indeed could be used in any non-bifurcated or stent only construction that require similar functionality.

Figure 20B:
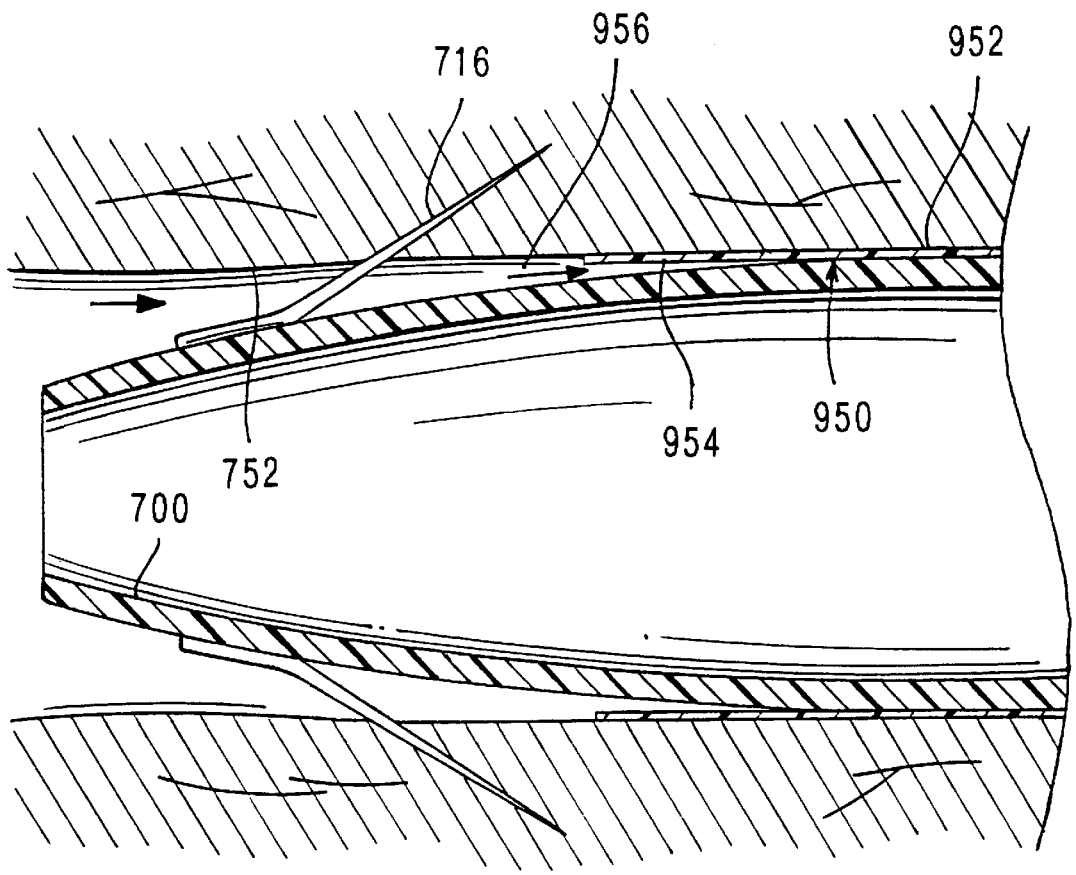
FIG. 20B is a longitudinal cross-sectional view of a generic tubular member with anchor and seal member deployed within an endolumenal space.

FIG. 20B further shows an implantable medical device with a tubular member, which is shown schematically and is preferably a stent-graft, with an anchor (716) and seal member (950) deployed into an endolumenal space. This is shown to further illustrate the effect an anchor may have on the tubular member wall when it is impinged into the artery wall. Much like a lever, the anchor pushes the tubular member wall out from the artery wall and creates a leak path. Sealing member (950) has flange (954) and first cuff end (952) in position to occlude such leak passageways.

In addition to maintaining a good contact with the vessel lumen walls, the components of the stent-graft must make sufficient contact with each other such that the separate modules stay attached and do not leak at their engagement interface. The inventive stent-graft shown in FIG. 21 illustrates several important features designed to effectuate a leak-free and positionally stable seal at the interface between the receiving lumen (703) of the main body component (700) and contralateral leg component (730).

Figures 21, 22, 23:
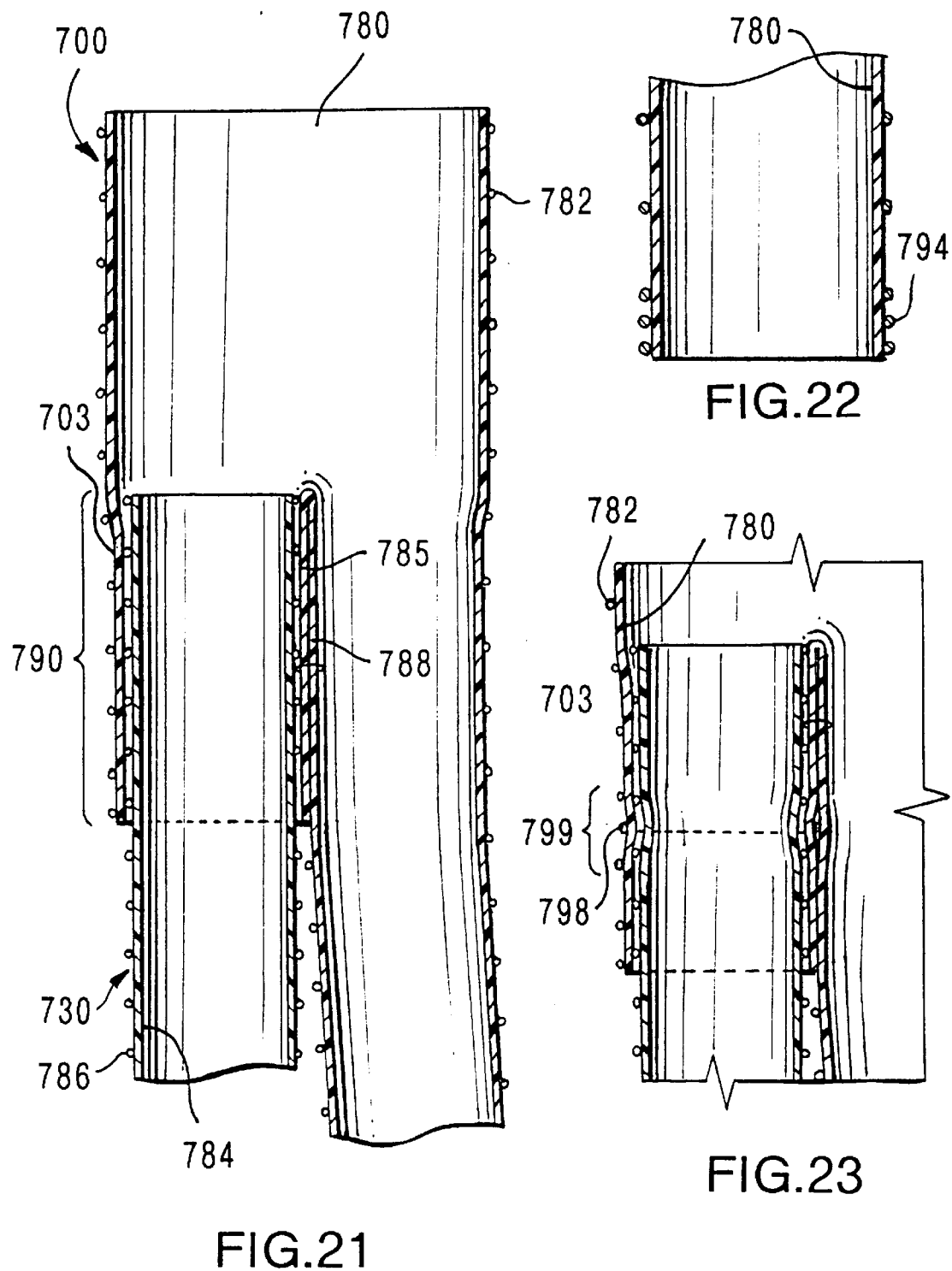
FIG. 21 is a cross-section view of the stent-graft tubular member taken along section line 21—21 depicted in FIG. 17B.
FIG. 22 is a cross-section view of the stent-graft depicted in FIG. 17A, taken along section line 22—22.
FIG. 23 is an enlarged partial cross-sectional view of the contralateral leg connection depicted in FIG. 22.

FIG. 21 shows a partial cross-section of the assembled stent-graft. The contralateral leg component (730) has been inserted into the receiving lumen (703) of the main body component (700). This cross-sectional view shows clearly that the main body component (700) includes a main body graft member (780) and a main body stent member (782). The contralateral leg component (730) includes a contralateral graft member (784) and a contralateral stent member (786).

At the interface between the contralateral leg component (730) and the receiving lumen (703), the assembly provides for an extending sealing region (790). Preferably the extended sealing region (790) consists of a generally cylindrical interfering friction fit between the outside diameter of the contralateral leg component (730) and the inside diameter of the receiving lumen (703). That is the natural or resting outside diameter of the self expanding contralateral leg component (730) would be larger than the natural inside diameter of the receiving lumen (703). Thus the forces created by the interference act to seal the two components and also serve to resist movement of the two components.

The type of generally cylindrical extended sealing region just described has many advantages. First, it allows for the stent and graft structures in the extended sealing region (790) to be constructed of relatively simple generally cylindrical elements that are easily manufactured. Because the extended sealing region (790) extends over a large length it necessarily has a large surface area to effectuate sealing between the components. This larger sealing area typically provides that multiple turns of the stent structures will be engaged in an interfering and thus sealing relationship.

In one preferred variation, the extended sealing region has a length in excess of one-half of the diameter of the receiving lumen (703), more preferably the length is greater than the diameter of the receiving lumen (703), and most preferably the length is more than 2 times the diameter of the receiving lumen (703).

Because the manufacturing tolerances of the simplified shapes are easily controlled and because the engagement of the extended sealing region (790) is quite large, a highly reliable joint is formed between the modular components. Even so it may be desirable to create one or more localized zones of increased interference to increase the sealing capability and positional stability.

Localized zones of interference may be created in a number of ways. In a preferred variation, an annular ring of decreased diameter is formed within the receiving lumen. Such a localized decreased diameter causes a greater interference with the outside diameter of the contralateral leg component in a localized area while the remainder of the engagement with the receiving lumen is subject to the general interference friction fit described above.

One way of creating a localized decreased diameter is illustrated in FIG. 23 which shows a partial cross-section of the extended sealing region (790). A zone of reduced diameter (799) is created by placing an anchoring ring (798) between the graft member (780) and the stent member (782) of the receiving lumen (703). The anchoring ring may be made from any polymeric or wire material, preferably a material that will not inhibit the receiving lumen from self-expanding to an open position. Most preferably the material is a suture material, typically ePTFE.

Figure 24:
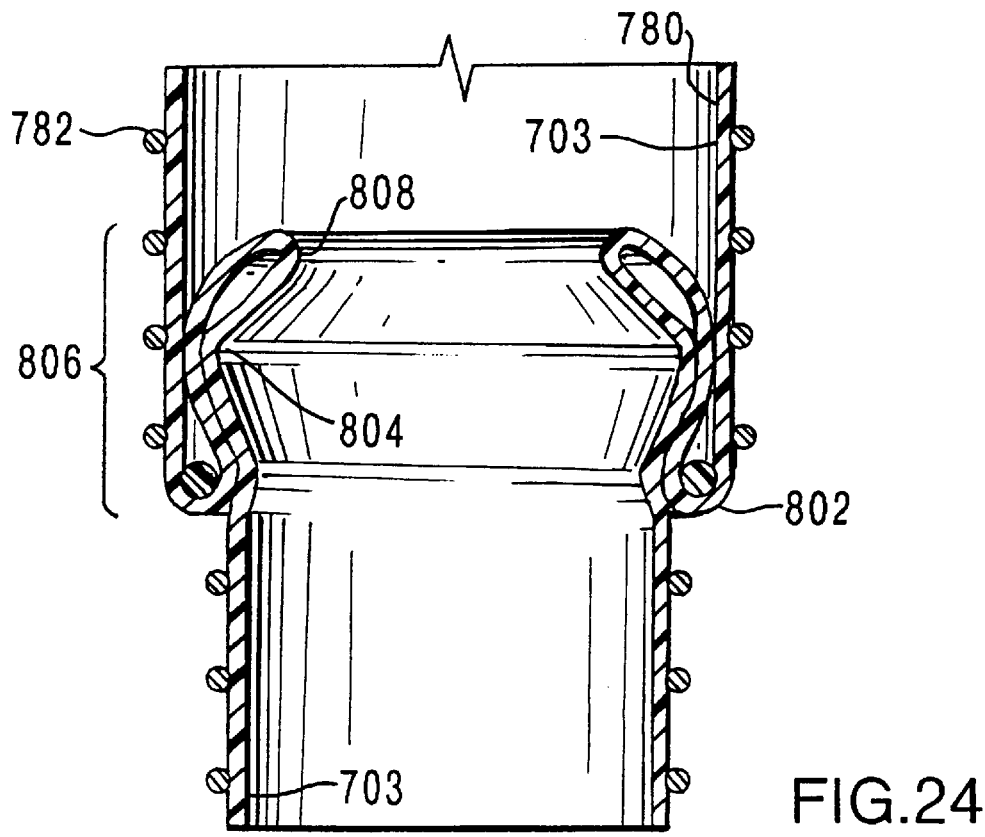
FIGS. 24 and 25 are enlarged partial cross-sectional views of alternative constructions of the receiving lumen.
Figure 25:
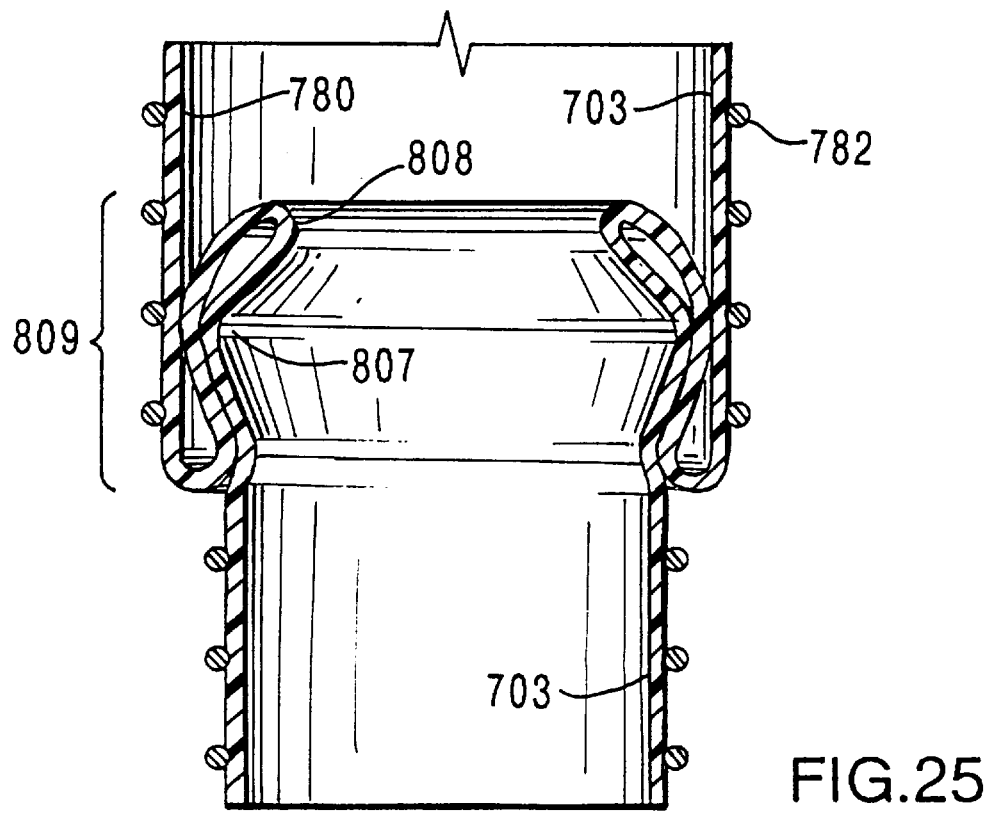

Alternately, localized zones of decreased diameter may be created as shown in FIGS. 24 and 25 by folding a portion of the graft member (780) back up into the receiving lumen (703). In FIG. 24, the zone of reduced diameter (806) is formed by creating a folded flap (808) of the graft material (780) around an anchoring ring (802). The flap is heat bonded in place roughly at a location (804) as shown. In FIG. 25, the zone of reduced diameter (809) is formed of flap (808) and heat bonded roughly at a location (807) in a similar manner but without any anchoring ring. The localized interference using these methods tends to cover a larger area and the flap (808) provides a more flexible member to seal against the outside diameter of the contralateral leg component (730).

One further aspect of ensuring a good seal between the stent-graft components involves the use of a scalloped stent-graft construction at the distal end of the contralateral leg component (810). To create this scalloped construction, the graft material between the apexes of the stent member is removed on the last turn of the stent. For example scallop (812) may be formed by removing (or folding under) the graft material from between a first apex (814) and an adjacent apex (816).

Figure 27A:
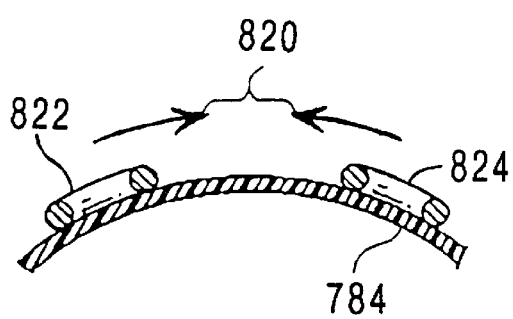
FIGS. 27A and 27B are cross-sectional views taken along section line 27A—27A as shown in FIG. 17A depicting a free state and a forced state respectively.
Figure 28A:
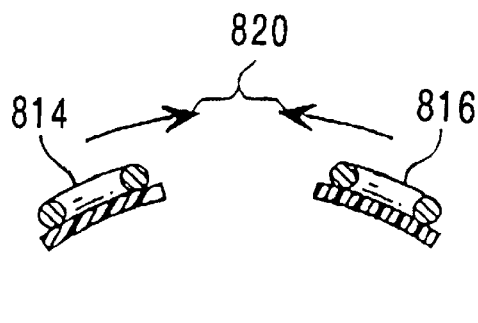
FIGS. 28A and 28B are cross-sectional views taken along section line 28A—28A as shown in FIG. 26 depicting a free state and a forced state respectively.
Figure 27B:
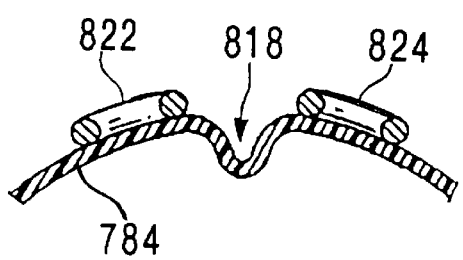
Figure 28B:
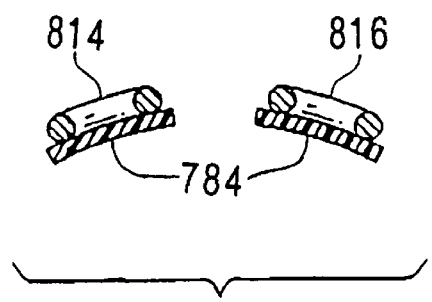

The advantage of using a scalloped arrangement are illustrated in FIGS. 27A through 28B. FIG. 27A shows a cross-section of the fully expanded contralateral leg component (730) having an unscalloped construction. A first apex (822) and an adjacent apex (824) have continuous graft material (784) in the area between them. If the apex (822) and the adjacent apex (824) are forced together in the directions of the arrows (820), the graft material (784) forms a buckle or wrinkle (818) which is a potential leak path or is a potential site for thrombogenic material to build up as seen in FIG. 27B. The scalloped construction shown in FIGS. 28A and 28B, on the other hand, have no graft material between the first apex (814) and the adjacent apex (816) and therefore when forced together do not form a graft material wrinkle.

The wrinkle (818), mentioned above may also be formed when the stent-graft is not allowed to expand to its complete diameter. For instance it is quite common that the receiving lumen or vessel wall internal diameter is smaller than the fully expanded stent-graft outer diameter. In fact, in order to achieve complete stent-graft deployment with secure positioning and minimal leakage flow, oversizing a stent-graft to the vessel is often a desirable design choice. This being the case, it should be clear that the scalloped construction may alternately be used at any of the terminal openings of the main body component or the contralateral leg component. Preferably, the distal end (702) of the main body component (700) also has this scalloped construction as shown in FIGS. 17A and 17B.

Figures 29A, 29B:
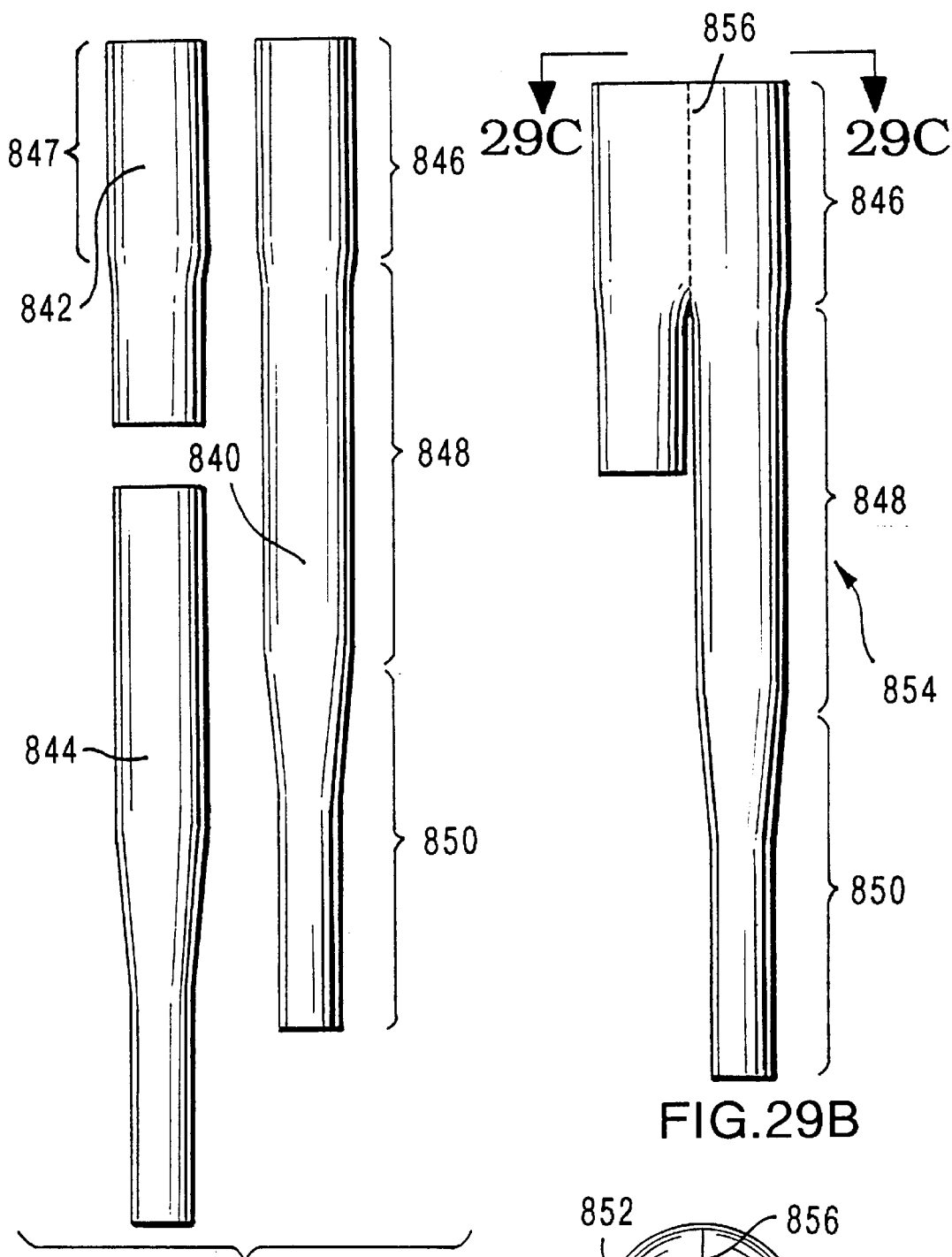
FIG. 29A is a front view of the unassembled components of a variation of the graft element to be combined with a stent member to form a tubular member variation for use with the current invention.
FIGS. 29B and 29C are respectively the front view and top view of the assembled graft elements.
Figure 29C:
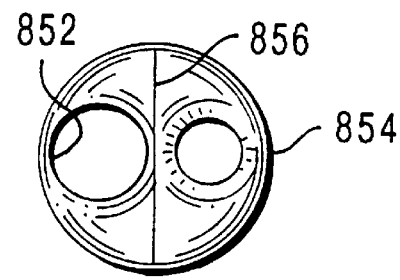

In the previous discussion we have referred generally to a stent-graft that includes a graft member. While the construction of such straight stent grafts are discussed at length above, the construction of a bifurcated graft member is illustrated in FIGS. 29, 30A and 30B. A bifurcated graft member suitable for construction of the main body component (700) discussed above is generally formed of two graft members: the ipsalateral tapered graft (840) and the contralateral tapered graft (842). The separate contralateral leg graft component (844) is a straight or tapered section and may be formed according to the principles discussed in the first section above.

The ipsalateral tapered graft (840) has three sections which are separated by tapers. A top section (846), a middle section (848), and a bottom section (850). The body component graft (854) is formed by heat bonding the top section (846) of ipsalateral tapered graft (840) to the top section (847) of contralateral tapered graft (842). This heat bonding forms a common septum (856) which in a preferred variation is subsequently cut away to produce a smooth bifurcation. Cutting away the septum material prevents fluid flow disturbance or blockage that could result from deviation of the septum. Such deviation is caused by the fluid pressure and is aggravated if the stent-graft is radially compressed in a manner which causes the septum to become loose or no longer taut.

In another embodiment, a graft section may be constructed in the manner illustrated in FIGS. 30A and 30B. According to this embodiment, the body component graft (867) is constructed from two pieces. A tubular graft section (860) is bent into a 'U-shape'. A top hole (864) is formed by notching the top of the 'U-shape'. Upper graft section (862) is placed over the top hole (864) of tubular graft section (860). The two pieces are bonded together at the bonding interface (866). Preferably, the two graft pieces are heat bonded while supported by interior mandrels (not shown) to obtain the desired shape and smooth interior. However, upper graft section (862) may be attached to the tubular graft section (860) at the bond interface (866) in any manner that provides a sufficient leak-free seal. For example, the components may be sutured together or adhesive bonded.

Figure 31C:
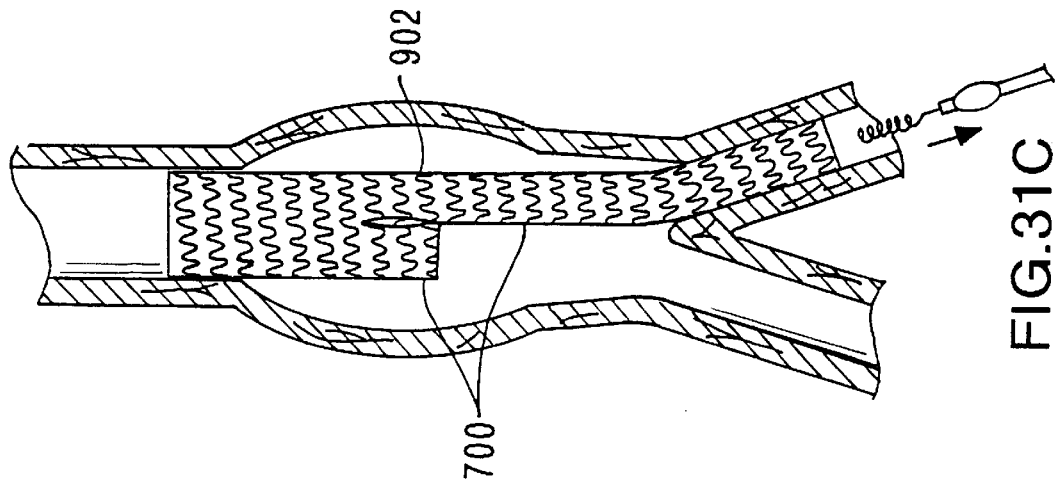
FIGS. 31A through 31E diagrammatically show the deployment of the two components of a bifurcated stent-graft constructed according to the principles of the present invention using a type of restraining member for deployment.

In use, the modular bifurcated stent-graft is typically delivered percutaneously through the vasculature of the body. Preferably the prosthesis is delivered by way of a restraining member as described in detail above. FIGS. 31A though 31E diagrammatically illustrate deployment of a bifurcated stent-graft with a restraining member (902) using a percutaneous catheter assembly. Referring to FIG. 31A, a multilumen catheter assembly (928) has been inserted to a selected site within a body lumen. The main body component (700) of a bifurcated stent-graft is held in a compressed state about a guidewire (926) and a guidewire lumen (929) by a restraining member (902) and a coupling member (906). The collapsed main body component (700) is held axially in place prior to deployment by a distal barrier (930) and a proximal barrier (932). The distal (930) and proximal (932) barriers are typically affixed to the guidewire lumen (929). The coupling member (906) extends through the eyelets (920) of the restraining member (902) forming chain knots and into the multilumen catheter (928).

FIG. 31A shows advancement of the multilumen catheter (928) with the distally located main body component (700) and the restraining member (902) into implantation position, typically at the bifurcation of a major vessel. During deployment it is critical that the surgeon align the main body component (700) so that the ipsalateral leg (726) will extend down one branch of the bifurcated vessel, and so the receiving hole (704) and the receiving lumen (703) will be lined up with the other branch of the bifurcated vessel so as to receive the contralateral leg component (730).

One way of facilitating this alignment is to provide radiopaque markers so that the surgeon may readily determine the rotational position of the main body component (700) prior to deployment or release from the restraining member (902). In a preferred variation, a long marker (934) is located on the contralateral side of the compressed assembly and a shorter marker (936) is placed on the ipsalateral side. Preferably these markers are placed on the stent prior to compression but may alternatively be part of the restraining member. Having one marker of a different length allows the surgeon to identify the orientation of both the ipsalateral leg and the receiving lumen relative to the bifurcated vessel.

Once the assembly is properly aligned and positioned for implantation, the coupling member (906) is pulled and the restraining member (902) begins to release the implant, typically at the distal end first. In the preferred embodiment, the restraining member (902) is located down the side as shown because it is less likely to interfere with deployment of the receiving lumen (703).

Figure 31B:
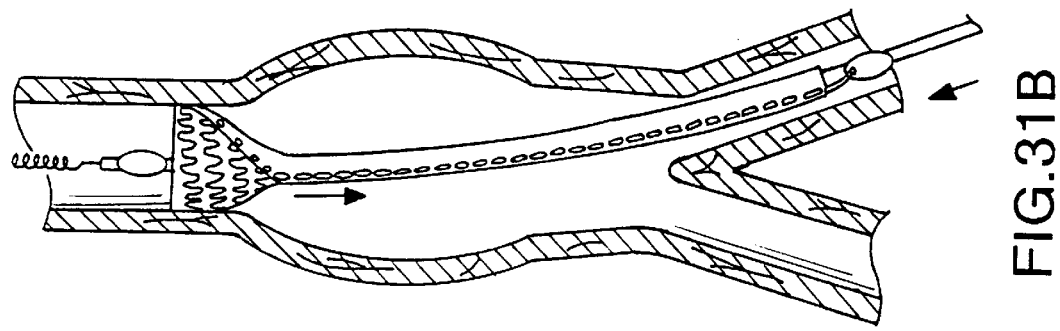
Figure 31A:
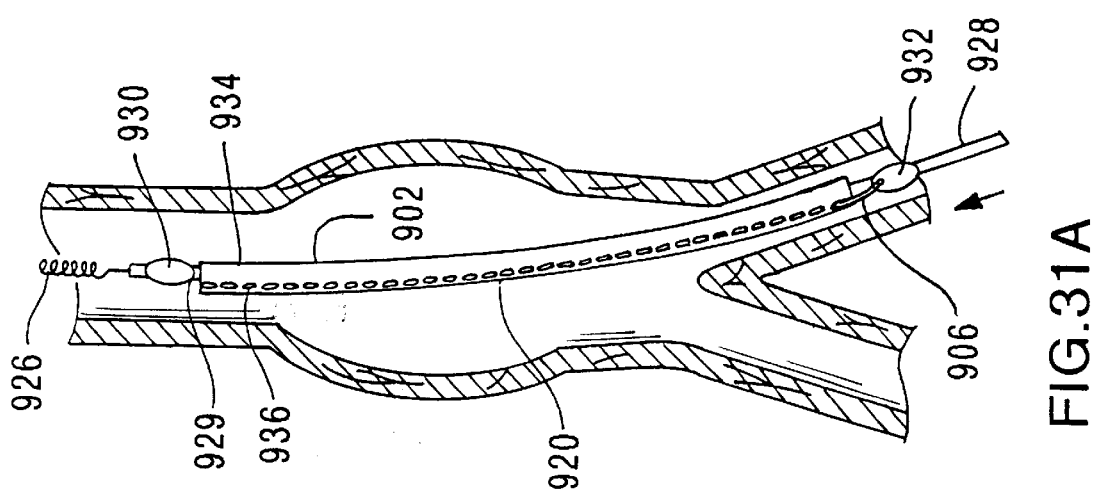

FIG. 31B shows the main body component (700) radially expanding as the coupling member (906) is retracted through the eyelets (920) of the restraining member (902) and into the catheter assembly (928). In the preferred embodiment, the restraining member (902) has been fixedly attached to the main body component (700) with a number of sutures along the length of the main body component to prevent any relative longitudinal movement between the implanted prosthesis and the restraining member (902). The restraining member may optionally employ a retracting or pull-down mechanism as described at length above.

FIG. 31C shows the main body component (700) and the restraining member (902) in final implantation position at the vessel bifurcation after the guidewire (926) and the catheter assembly (928) have been retracted.

Figure 31E:
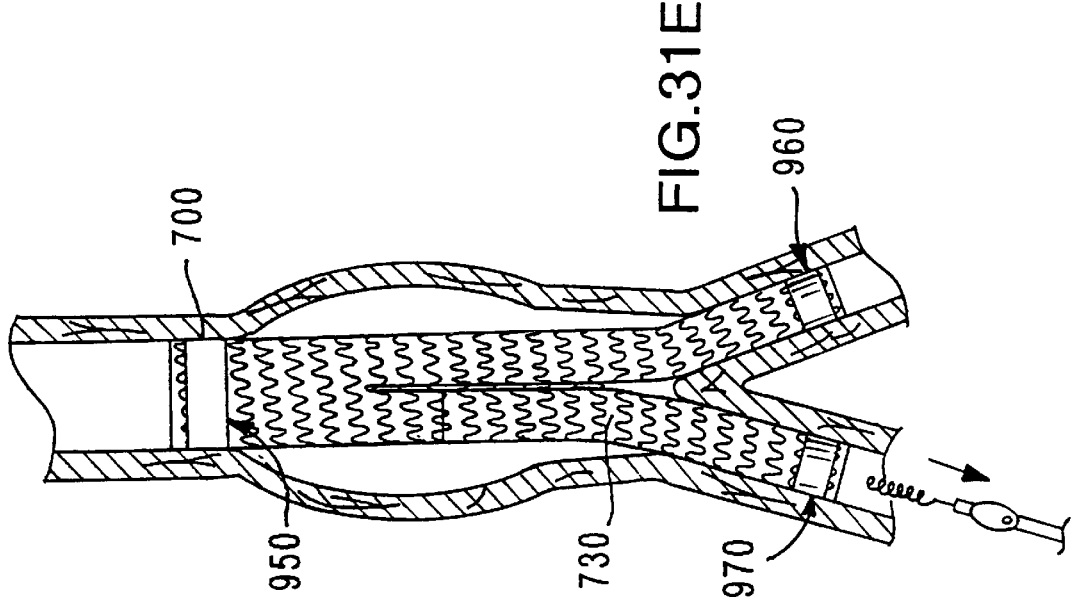
Figure 31D:
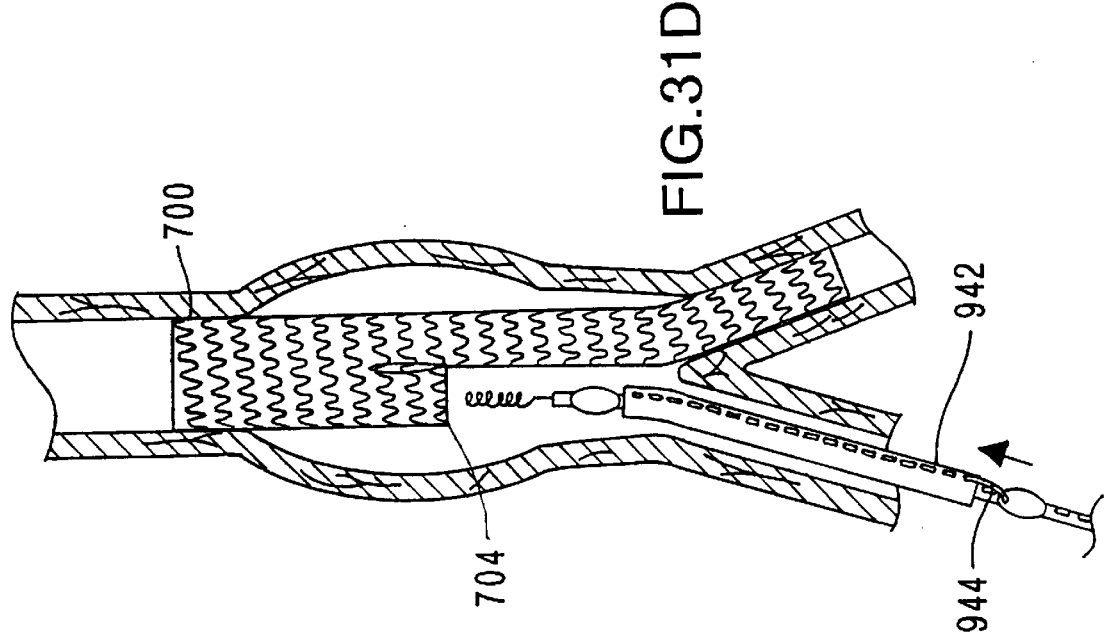
Figure 32A:
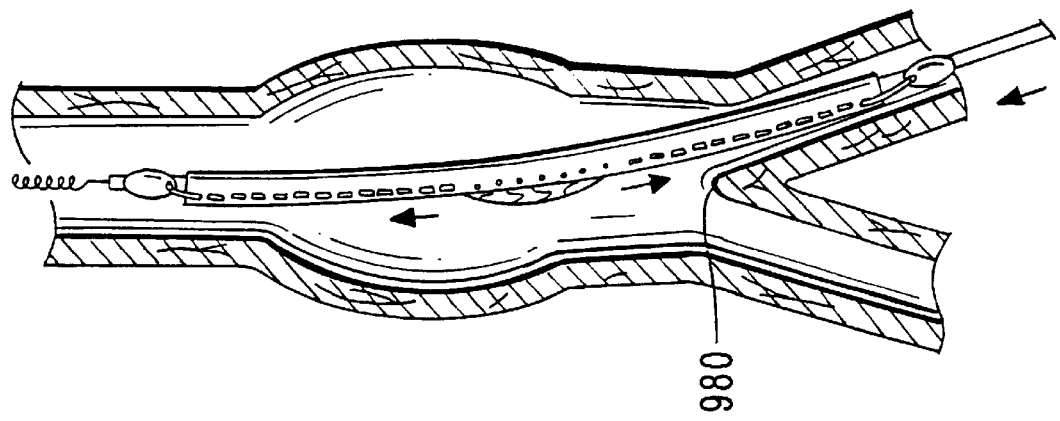
FIGS. 32A through 32D diagrammatically show the deployment of the two components of a bifurcated stent-graft constructed according to the principles of the present invention using an alternate type of restraining member which provides release from the middle portion of the implant outward toward the implant ends.
Figure 32B:
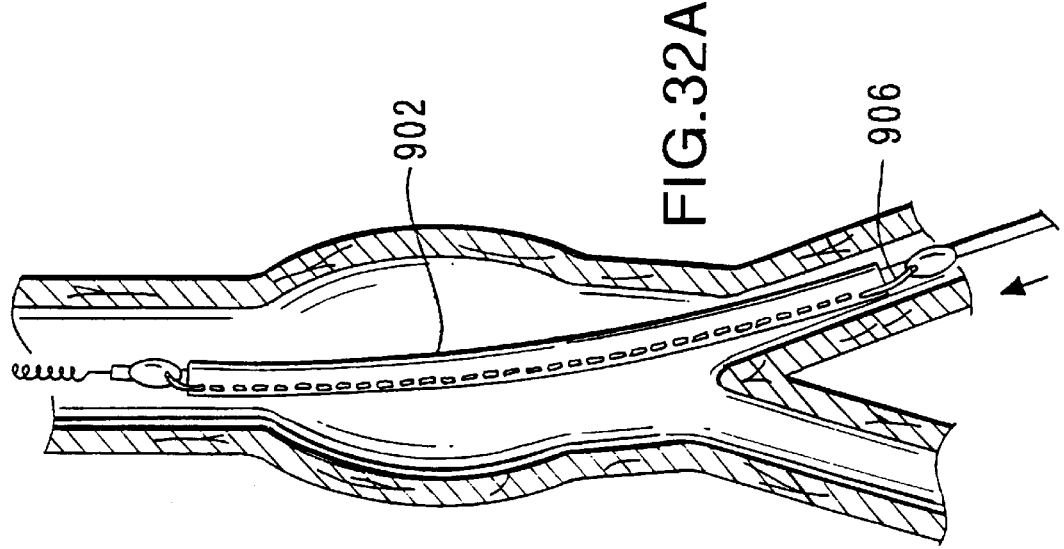
Figure 32D:
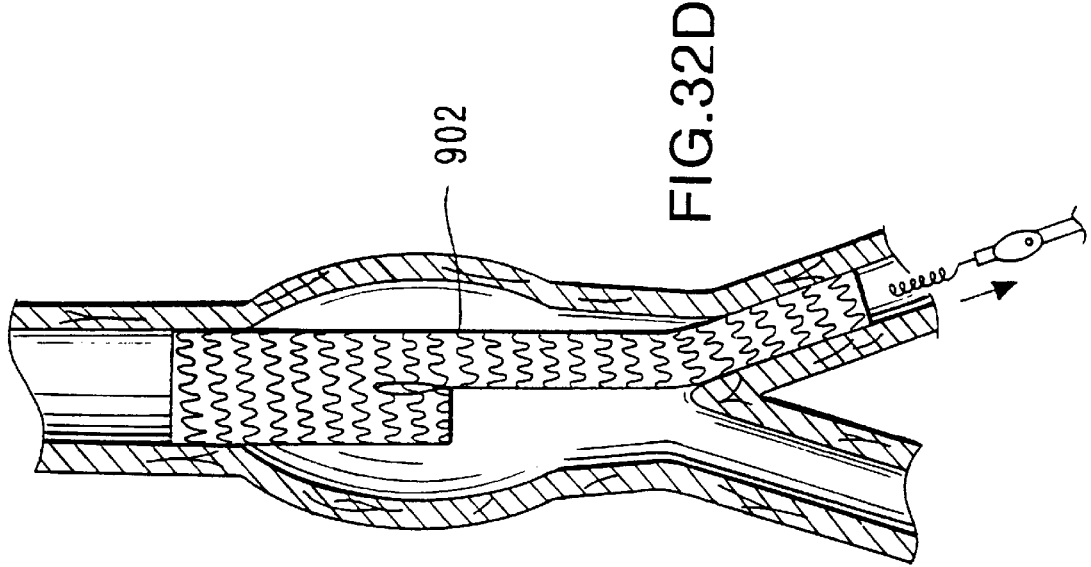
Figure 32C:
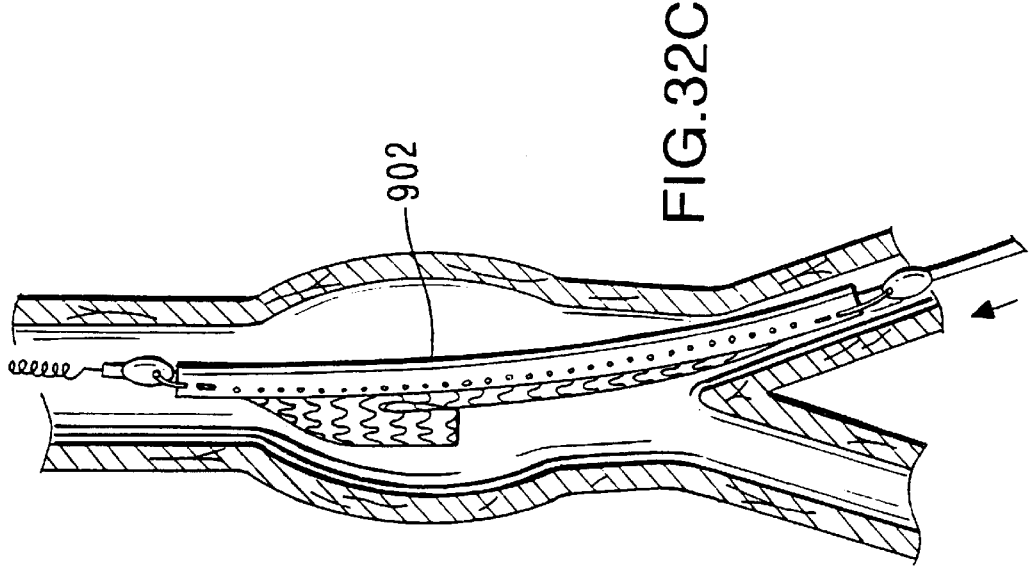

FIG. 31D shows the contralateral leg component (730) being delivered to the contralateral receiving hole using a restraining member (942). The procedure for positioning and releasing the contralateral leg component (730) is the same as that described above for implantation of a generally cylindrical stent-graft except that certain radiopaque markers may be employed to ensure its prosper position relative to the bifurcation point (728) of main body component (700).

Radiopaque markers may be located, for example, to indicate the position of the receiving hole (704), the distal end (734) of the contralateral leg component (730), and the bifurcation point (728) of the main body component (700). These markers serve to indicate the position of the contralateral leg component as it enters the receiving hole (704) and its ultimate position relative to the receiving lumen (703) which begins at bifurcation point (728). In a preferred variation illustrated in FIG. 22, the radiopaque wires (794) may be heat bonded or imbedded into the graft material (780) around the periphery of the receiving lumen. Such radioopaque wires could be used in other places such as the contralateral leg component lumen, the ipsalateral leg lumen or the lumen at the distal end of the main body component (700).

FIG. 31E shows the assembled bifurcated stent-graft in its final implantation state with the contralateral leg component expanded into and engaged with the receiving lumen of the main body component (700).

FIGS. 32A through 32D diagrammatically show the same stent or stent-graft components being deployed except that the restraining member (902) is released from the center out towards as the coupling member (906) is retracted. This may provide more accurate placement relative to the bifurcation point of the vessel instead of relative to the distal end as with end release.

Seal member (950) is further shown throughout FIGS. 17A–32D where its inclusion is appropriate to illustrate how the seal member combines with these stent-graft tubular member variations to result in the implantable medical device of the present invention.

For example, FIGS. 19 and 20A show seal member (950) secured to the outer surface of the stent-graft member adjacent to apex anchors (716), which may be proximally positioned adjacent to such anchors located on the distal main body end of a bifurcated stent graft. Seal member (950)

is shown as an occlusive cuff which preferably circumferentially envelops both the stent member and the graft member of the stent-graft tubular member. Seal member (950) has a first cuff end (952) secured to the outer surface of the stent-graft, and also has a second cuff end (954) that is unsecured and extends distally toward apex anchors (716), forming a flange over the struts of the stent member. In this orientation relative to the longitudinal axis of the stent-graft, seal member (950) forms a one-way valve to occlude flow over the stent-graft and in the direction from the stent-graft end and toward the central portion of the stent-graft, for instance toward an aneurysm adjacent the bifurcation.

One preferred construction for seal member (950) in the variations shown in FIGS. 19 and 20A may be similar to the preferred construction for the tape member used in constructing the stent-graft tubular member, as is provided in reference to FIG. 6 above.

In general, a thin walled ePTFE tape is used for seal member (950) similarly as that for tape member (128), shown variously in the previous figures. The tape used for seal member (950) is adhered to the outer surface of the stent-graft, including over tape member (128), described previously for bonding the stent and graft members. Seal member (950) has an inner surface constructed of a similar material for either the outer surface of the tape member (128) or the outer surface of the graft-member (124), depending upon which surface the seal member is desirably adhered. In one preferred mode, the construction of seal member (950) has a width along the longitudinal axis of the stent-graft of about 2 cm, wherein first end portion (952) comprises about 1 cm and second end portion (954) comprises about 1 cm.

First cuff end (952) is bonded to the stent-graft outer surface and second cuff end (954) is not, in order to form the unadhered flange to function as a one-way valve against peri-stent-graft flow. Seal member (950) may be selectively adhered along its length in this manner by providing a variable inner surface to the seal member such that, upon heating, only the surface in the region of first cuff end (952) bonds to the outer surface of the stent-graft. For example, the inner surface of seal member (950) may have an FEP liner in the region of first cuff end (952) but not in the region of second cuff end (954). In this case, upon contacting an outer surface of the stent-graft that has a uniform FEP outer surface, only first cuff end (952) may be heat secured thereon.

Alternatively, seal member (950) may have a uniform inner surface, such as constructed of FEP, and a variable outer surface, such as with a selective portion of FEP, may be provided either on the tape member (128) or on the graft member (124) in the region where the heat bonding of seal member (950) is desired. Still further, seal member (950) may have a uniform surface and may be positioned over tape member (128) and graft member (124) so that variability between the outer surfaces of tape member (128) and graft member (124) causes a selective bonding with the first cuff end (952) over one of those surfaces.

Further to the construction of seal member (950), the particular wall thickness of the tape which may be used for this component should desirably be as thin as possible to functionally provide the flange-one-way-valve function for that member. This is because, since seal member (950) is over the outer surface of the other stent and graft components of the stent-graft, seal member (950) is believed to be the profile-limiting feature of the overall assembly. Therefore, in a particular design, seal member (950) may desirably be a thinner wall than for the tape member used to construct the stent-graft described in reference to FIG. 6.

Further referring to the particular constructions and related methods just described for adhering seal member (950) to the outer surface of the underlying stent-graft, it should be apparent to one of ordinary skill in the art that the desired construction and heat securing technique for seal member (950) is premised upon the theory that, where one polymer meets a like polymer (such as FEP meeting FEP), heating under proper conditions will allow for a selected heat bond. The present invention, however, should not be construed as limited to these particularly described conditions, but instead should be considered to more broadly encompass any suitable means for securing a seal member to the outer surface of a given tubular member, as would be apparent to one of ordinary skill, and as is provided previously with reference to FIG. 1.

Further to the detail shown in FIGS. 19 and 20A, a plurality of circumferential strut spaces (956) are also shown between the struts of the stent member. It is believed that these spaces may provide a path for leakage flow around the outer surface of the graft member and along the outside of the stent-graft. Second cuff end (954), however, captures such leakage flow beneath its flange, which can not propagate along the outer surface of the stent-graft because first cuff end (952) is secured to the outer surface of that stent-graft. In other words, flow over the stent-graft and into an aneurysm is occluded.

Furthermore, when apex strut (716) is anchored into the wall of abdominal aortic artery (752), as shown in FIG. 20B, it has been observed that the portion of main body (700) at and adjacent to the apex strut (716) can be forced away from the artery wall particularly in case of calcified tissue. This action causes a separation (956) between the outer surface of main body (700) and the artery wall, which separation is believed to create a leakage flow path. The flange of seal member (950) captures that flow and occludes it from propagating into the aneurysm (758).

FIG. 31E further shows seal member (950) on a stent-graft in combination with additional seal members (960, 970), which are located adjacent the ends of ipsalateral and contralateral legs (726,730), respectively, of the modular stent graft assembly.

It is believed that distal leakage flow around the legs of bifurcated stent-grafts may often be a major contributing component to overall leakage flow into the aneurysms which are intended to be protected by such stent-grafts against flow. Seal members (960,970) are beneficially intended to occlude such distal leakage.

It should be further appreciated that the present invention contemplates seal members (950), (960), and (970), as well as combinations thereof, secured to the outer surfaces of the tubular member designs shown in FIGS. 17A, 18, 31C–D, or 32A–D. Furthermore, any sufficient seal member, such as those provided in the above described embodiments and variations thereof, may be used with these stent-graft variations and fall within the scope of the invention. For example, either the flange occlusion cuff variations described, or even an expandable hydrophilic member, may be used with the bifurcated stent-graft shown in these Figures, such as FIG. 31E, and fall within the scope of the present invention.

Figure 26:
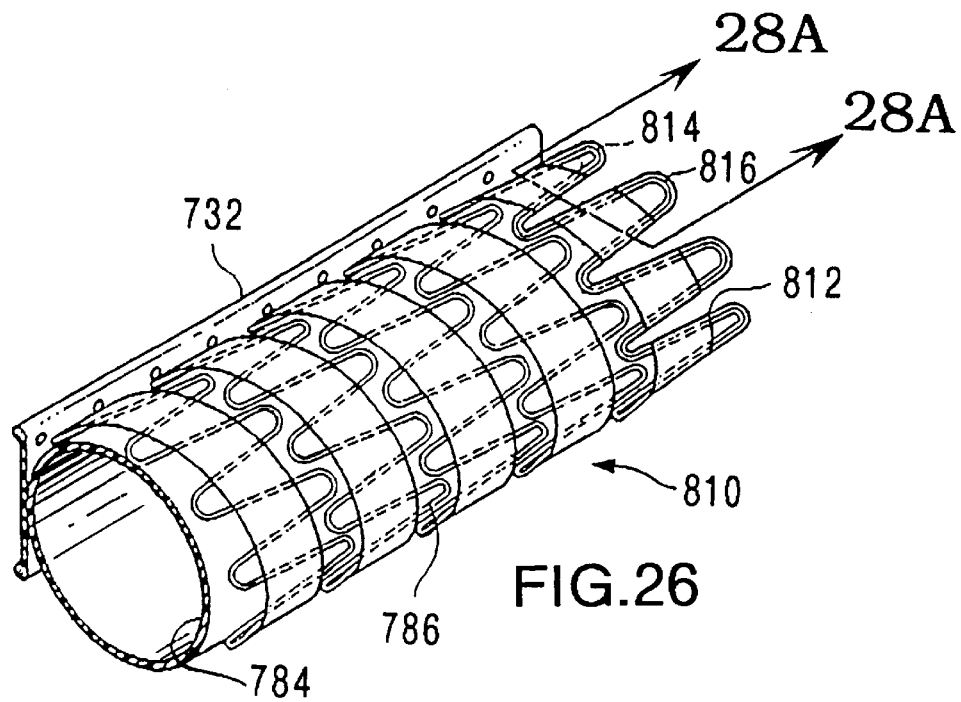
FIG. 26 is a partial perspective view of an alternate scalloped construction of the proximal region of the contralateral leg component.

In a further variation, a seal member such as seal member (950) shown variously in the figures, may be secured over the distal end of contralateral leg component (810) in a modular stent-graft assembly, such as shown at (810) in FIG. 26. The potential leak path through wrinkle (818) of the graft member (FIG. 27B) is formed by oversizing the leg component for coaxial engagement with the other modular graft component. Seal member (950) blocks the leak path through wrinkle (818), which would otherwise allow flow out of the lumen of the stent-graft and into the surrounding endolumenal space.

The wrinkle (818) is caused by a similar condition to that described earlier with reference to oversizing graft members relative to engage arterial walls, such as is shown in and described in reference to FIG. 3. In fact, it is quite common that the receiving lumen or vessel wall internal diameter is smaller than the fully expanded stent-graft outer diameter. In order to achieve complete stent-graft deployment with secure positioning and minimal leakage flow, oversizing a stent-graft to the vessel is often even a desirable design choice. Therefore, all cases of stent-graft oversizing and wrinkling may benefit from the seal member design of the current invention.

While this invention has been described with reference to illustrative embodiments, this description is not intended to be construed in a limiting sense. Various modifications and combinations of the illustrative embodiments, as well as other embodiments of the invention will be apparent to persons skilled in the art upon reference to the description. It is therefore intended that the appended claims encompass any such modifications or embodiments.

What is claimed is:

1. A device comprising:
   a self-expanding substantially tubular stent-graft, said stent-graft having an outer surface and upstream and downstream ends;
   a seal member secured to the outer surface of said stent-graft adjacent said upstream end, said seal member comprising an occlusive cuff having a downstream cuff end secured to said outer surface and an unsecured upstream cuff end actuatable to form a seal over said outer surface; and
   a plurality of anchor members spaced around the outer surface of said stent-graft upstream of said seal member, said anchor members having first anchor end portions secured to said outer surface and second anchor end portions extending radially outward from said outer surface.

2. The device of claim 1 further comprising a second seal member secured to the outer surface of said stent-graft adjacent said downstream end, said second seal member comprising an occlusive cuff having an upstream end secured to said outer surface and an unsecured downstream cuff end actuatable to form a seal over said outer surface.

3. The device of claim 2 further comprising a second plurality of anchor members spaced around the outer surface of said stent-graft downstream of said second seal member, said anchor members having first anchor end portions secured to said outer surface and second anchor end portions extending radially outward from said outer surface.

4. The device of claim 1 wherein said anchor members constitute integral extensions of said stent-graft.

5. The device of claim 1 wherein said seal member is formed from a polymeric material.

6. The device of claim 5 wherein said polymeric material is a fluoropolymer.

7. The device of claim 6 wherein the fluoropolymer contains polytetrafluoroethylene.

8. The device of claim 6 wherein the fluoropolymer comprises expanded polytetrafluoroethylene.

9. The device of claim 1 wherein said self-expanding stent-graft is a bifurcated stent-graft having the bifurcation of the downstream end.

10. The device of claim 1 wherein said stent-graft comprises a tubular stent portion coaxially coupled with a tubular graft portion, said stent member being defined by a helically arranged undulating member containing multiple turns about a common longitudinal axis, said undulating member containing a plurality of undulations.

11. The device of claim 10 wherein said undulating member is formed from a nickel-titanium alloy.

12. The device of claim 10 wherein said graft member is formed from a polymeric material.

13. The device of claim 12 wherein said polymeric material is polytetrafluoroethylene.

14. The device of claim 13 wherein the polytetrafluoroethylene is expanded.

15. The device of claim 10 wherein said undulations in said multiple turns of said undulating member are in a phased relationship.

16. The device of claim 15 wherein said undulations have varying amplitudes.

17. A system comprising the device of claim 1 further comprising a sheet of material proportioned to contain the device in a collapsed state; and
   a coupling member for releasably coupling portions of the sheet to one another to maintain said device in a collapsed state for delivery to a vessel lumen.

18. A device comprising:
   a self-expanding stent-graft having an outer surface, an upstream end portion comprising a substantially tubular structure having a single lumen, and a downstream end portion comprising multiple leg portions, each said leg portion terminating in a downstream end and comprising a substantially tubular structure having a separate lumen in communication with the single lumen;
   a seal member secured to the outer surface of said stent-graft adjacent said upstream end, said seal member comprising an occlusive cuff having a downstream cuff end secured to said outer surface and an unsecured upstream cuff end actuatable to form a seal over said outer surface; and
   a plurality of anchor members spaced around the outer surface of said stent-graft upstream of said seal member, said anchor members having first anchor end portions secured to said outer surface and second anchor end portions extending radially outward from said outer surface.

19. The device of claim 18 wherein at least one of said leg portions further comprises an additional seal member secured to the outer surface of said stent-graft adjacent said downstream end of said at least one leg portion, said seal member comprising an occlusive cuff having an upstream end secured to said outer surface and an unsecured downstream cuff end actuatable to form a seal over said outer surface.

20. The device of claim 19 further comprising an additional plurality of anchor members spaced around the outer surface of said stent-graft downstream of said additional seal member, said anchor members having first anchor end portions secured to said outer surface and second anchor end portions extending radially outward from said outer surface.

21. The device of claim 18 wherein said downstream end portion includes first and second leg portions, said second leg portion being longer than said first leg portion.

22. The device of claim 21 further comprising a generally tubular extender leg adapted for engagement with said first leg portion.

23. The device of claim 22 wherein said self-expanding stent graft has an expanded and a collapsed configuration; and
   when said stent-graft is in said expanded configuration, the separate lumen of said first leg portion is adapted to receive therein an end portion of said extender leg.

* * * * *

UNITED STATES PATENT AND TRADEMARK OFFICE
CERTIFICATE OF CORRECTION

PATENT NO. : 6,015,431
DATED : January 18, 2000
INVENTOR(S) : Thornton, et. al.

It is certified that error appears in the above-identified patent and that said Letters Patent is hereby corrected as shown below:

In claim 9, col. 31, line 63, please delete "of" and insert therefor -- at --.

Signed and Sealed this

Fifth Day of December, 2000

Attest:

Q. TODD DICKINSON

Attesting Officer

Director of Patents and Trademarks